(12) United States Patent
Katz

(10) Patent No.: US 11,145,220 B2
(45) Date of Patent: Oct. 12, 2021

(54) SYSTEM FOR PEER-TO-PEER, SELF-DIRECTED OR CONSENSUS HUMAN MOTION CAPTURE, MOTION CHARACTERIZATION, AND SOFTWARE-AUGMENTED MOTION EVALUATION

(71) Applicant: SAVVY KNOWLEDGE CORPORATION, Calgary (CA)

(72) Inventor: Larry Katz, Calgary (CA)

(73) Assignee: SAVVY KNOWLEDGE CORPORATION

( * ) Notice: Subject to any disclaimer, the term of this patent is extended or adjusted under 35 U.S.C. 154(b) by 0 days.

(21) Appl. No.: 16/607,655

(22) PCT Filed: Apr. 18, 2018

(86) PCT No.: PCT/CA2018/050462
§ 371 (c)(1),
(2) Date: Oct. 23, 2019

(87) PCT Pub. No.: WO2018/195653
PCT Pub. Date: Nov. 1, 2018

(65) Prior Publication Data
US 2020/0211411 A1    Jul. 2, 2020

Related U.S. Application Data

(60) Provisional application No. 62/490,323, filed on Apr. 26, 2017.

(51) Int. Cl.
*G09B 19/00* (2006.01)
*G16H 20/30* (2018.01)
(Continued)

(52) U.S. Cl.
CPC ........ *G09B 19/0038* (2013.01); *A61B 5/1128* (2013.01); *A63B 24/0006* (2013.01);
(Continued)

(58) Field of Classification Search
CPC ...... G09B 19/0038; G09B 7/00; G16H 50/20; G16H 20/30; G16H 30/20; G16H 30/40;
(Continued)

(56) References Cited

U.S. PATENT DOCUMENTS

2011/0275045 A1    11/2011  Bhupathi et al.
2013/0028491 A1*   1/2013  Stephenson ............... G06T 7/73
                                                    382/128

(Continued)

FOREIGN PATENT DOCUMENTS

EP    3226229 A1    10/2017

OTHER PUBLICATIONS

ISA/CA—Canadian Intellectual Property OFFICE—International Search Report and Written Opinion of the International Searching Authority dated Jul. 11, 2018 for PCT/CA2018/050462 filed Apr. 18, 2018.

(Continued)

*Primary Examiner* — Masud Ahmed
(74) *Attorney, Agent, or Firm* — Daniel Polonenko

(57) ABSTRACT

A system for creating and/or using structured performance assessment tools for tracking and assessing the movement of a user includes a library having at least images of illustrative movement steps organized in a hierarchical structure, an imaging device, and an assessment device functionally coupled to the library and the imaging device. The assessment device is configured for selecting a set of movement steps from the library; capturing the movement of the user; concurrently displaying the selected set of movement steps and the captured movement of the user; and receiving an (Continued)

input representing an evaluation result of the captured movement of the user in comparison with the selected set of movement steps. The system can be used for self-evaluation, peer-to-peer evaluation, or consensus evaluation or coach-led evaluation of human motion, motion characterization, and software-augmented motion evaluation. The system allows the user to create content or access other users content.

20 Claims, 13 Drawing Sheets

(51) Int. Cl.
G16H 30/20 (2018.01)
G16H 30/40 (2018.01)
G06F 16/23 (2019.01)
A61B 5/11 (2006.01)
A63B 24/00 (2006.01)
G06K 9/00 (2006.01)
G09B 7/00 (2006.01)
H04N 7/18 (2006.01)

(52) U.S. Cl.
CPC ..... *G06F 16/2379* (2019.01); *G06K 9/00342* (2013.01); *G06K 9/00671* (2013.01); *G09B 7/00* (2013.01); *G16H 20/30* (2018.01); *G16H 30/20* (2018.01); *G16H 30/40* (2018.01); *H04N 7/188* (2013.01); *A63B 2024/0012* (2013.01); *A63B 2220/05* (2013.01); *A63B 2220/806* (2013.01)

(58) Field of Classification Search
CPC ............... G06F 16/2379; A61B 5/1128; A63B 24/0006; A63B 2024/0012; A63B 2220/05; A63B 2220/806; G06K 9/78; G06K 9/00758; G06K 9/00342; G06K 9/00671; H04N 7/188
See application file for complete search history.

(56) References Cited

U.S. PATENT DOCUMENTS

| 2013/0171601 | A1 | 7/2013 | Yuasa et al. | |
| 2013/0223707 | A1* | 8/2013 | Stephenson | G16H 20/30 382/128 |
| 2014/0257744 | A1 | 9/2014 | Lokshin et al. | |
| 2015/0139502 | A1* | 5/2015 | Holohan | G06T 7/75 382/107 |
| 2016/0098941 | A1* | 4/2016 | Kerluke | G06F 3/017 700/91 |
| 2017/0177930 | A1* | 6/2017 | Holohan | G16H 20/30 |

OTHER PUBLICATIONS

Canadian Intellectual Property Office—International Search Report and Written Opinion for PCT/CA2018/050462, dated Jul. 11, 2018.

* cited by examiner

SYSTEM FOR PEER-TO-PEER, SELF-DIRECTED OR CONSENSUS HUMAN MOTION CAPTURE, MOTION CHARACTERIZATION, AND SOFTWARE-AUGMENTED MOTION EVALUATION

CROSS-REFERENCE TO RELATED APPLICATIONS

This application claims the benefit of U.S. Provisional Patent Application Ser. No. 62/490,323, filed Apr. 26, 2017, the content of which is incorporated herein by reference in its entirety.

FIELD OF THE DISCLOSURE

The present disclosure relates generally to a system and method for motion capturing and characterization, and in particular to a system and method having a structured activity, skill, and skill-component map with peer-to-peer, self-directed or consensus evaluation for capturing and characterizing human motion for learning a performance skill such as a human movement skill.

BACKGROUND

Teaching a performance skill such as such as basketball dribbling, a gymnastics cartwheel, or a patient bed-to-bed transfer, in a class setting typically involves a proficient instructor demonstrating the skill, perhaps verbally highlighting a sequence of key components. This is typically followed by students attempting the skill in a directly supervised or an unsupervised manner.

The instructor will typically give feedback and input to the student to guide their learning. However, such feedback can be limited by the size of the class and the instructor's limited ability to observe all students simultaneously. So, drills may be performed by the students to reinforce a skill. The drills may be performed one at a time by the students so that an instructor can observe their performance and provide feedback. In this case, other students would typically wait for their turns.

Alternatively, students may perform the drill simultaneously and the instructor must try to observe all students sequentially and provide necessary feedback.

Better use of class time may be achieved by breaking a class into smaller groups to work on a drill. Students may then be able to observe their peers, but generally student peers would not be proficient at a skill, and their observations and comments may be inaccurate or incomplete.

Systems for teaching and learning a human motion skill are known. For example, there exist several systems providing comparison of a learner's movement with the movement of an expert such as a professional golf player. However, as these systems aim to condition the learner to directly mimic the movement of an expert, they only provide a simplistic approach to improvement and as a consequence, are mostly unsuccessful. For example, in baseball, there are several successful unorthodox pitching styles, so training a learner to simply mimic a pro-pitcher may not be appropriate.

US Patent Publication No. 2014/0081435, entitled "Connecting Players to Professional Athletes," to Wagner, discloses methods, systems, and computer program products for connecting players to professional athletes to receive evaluations from the professional athletes regarding the players' abilities within a sport. Such systems can be embodied as a website that allows a player to select one or more participating professional athletes to review a video of the player and to receive evaluations from the professional athletes regarding the abilities of the player. In this way, a player can receive an evaluation from an expert at the player's position or role within a sport. Such evaluations can be used by the player to continue improving his abilities, as well as to promote the player to recruiters at higher levels within the sport.

US 2014/0081435 requires a professional athlete to provide direct feedback to each participant. The assessment method disclosed therein comprises a star rating and unstructured comments.

US Patent Publication No. 2014/0308640, entitled "Method to Improve Skilled Motion Using Concurrent Video of Master and Student Performance," to Forman, et al., discloses a method to improve a skilled motion through holistic viewing, in-place and/or across a horizontal plane. The method involves a video camera, computer, and monitor system that displays a prerecorded video clip of a master's performance selected from a library of video clips recorded in a plurality of perspectives, and also displays a live video feed of a student performing the master's motion in the same perspective, controlled by placement of the video camera relative to the student. The method additionally discloses repeatedly providing slight variations of the master's skilled motion loop, and contains blacked-out segments so that the student may dynamically perform the selected motions both with and without the visual guidance of the master's performance. The video library includes tutorials on how and why to use specific digital video playback controls known to the art such as horizontal orientation, freeze frame, slow motion, as well as recording the live video to disk.

US 2014/0308640 requires an expert with mastery of the movement, and is for real-time execution by the learner against a recoded video of the expert. In other words, the method disclosed therein is a video-to-video method rather than a curriculum-to-video method. Further, US 2014/0308640 has no provision for evaluation criteria of measures of successful execution of the skill.

US Patent Publication No. 2008/0220941, entitled "Virtual Trainer System and Method," to Shaw, et al., discloses a system, apparatus, and method for managing health of different individuals by means of a virtual trainer over a network. Reference training data are made available to at least one individual. The exercise motions of the individual are recorded by using a plurality of sensing elements. The exercise motions of the individual are processed into user data. The user data is forwarded to a remote server via a user communication device. A virtual coach application is provided in the remote server that compares the reference training data with the user data and provides a corrective feedback to the individual. The corrective feedback to the individual may be provided on the user communication device such as a personal computer, digital assistant, mobile phone, and the like.

The system disclosed in US 2008/0220941 relies on sensors to communicate with an expert in a remote location who provides an evaluation to the learner. The system does not rely on structured curriculum for the expert to evaluate the learner and it is, therefore, incapable of self-evaluation, peer-evaluation, or consensus-evaluation.

US Patent Publication No. 2011/0270135, entitled "Augmented Reality for Testing and Training of Human Performance," to Dooley, teaches a system for continuously monitoring a user's motion and for continuously providing real-time visual physical performance information to the user while the user is moving. The system disclosed therein enables the user to detect physical performance constructs that expose the user to increased risk of injury or that reduce the user's physical performance. The system includes multiple passive controllers for measuring the user's motion, a computing device for communicating with wearable display glasses, and the passive controllers to provide real-time physical performance feedback to the user. The computing device also transmits physical performance constructs to the wearable display glasses to enable the user to determine if his or her movement can cause injury or reduce physical performance. This system only provides performance feedback concurrent with the human movement.

SUMMARY

With recognition of the problem of efficiently and effectively learning physical tasks or physical performance without direct supervision by an expert, this disclosure provides a system and method having a structured activity, skill, and skill-component map together with peer-to-peer, self-directed, or consensus evaluation criteria.

In some embodiments, the system disclosed herein allows peer-to-peer learning or self-directed learning without a requirement for an expert's participation or inputs. The system comprises a structured human movement library with video, text, annotation, still images, audio, or combinations thereof, and is suitable for all forms of human movement. The system facilitates users in learning and achieving competence with desired skills rather than direct mimicry of an expert performing those skills.

In some embodiments, the disclosed system may run on a tablet computing device. In some alternative embodiments, the system may incorporate virtual reality or augmented reality environments.

In some embodiments, the disclosed system may include a structured activity library so that individual skill components can be assessed by a relatively unskilled peer.

In some embodiments, the disclosed system is suitable for continuous monitoring of a user's motion and providing subsequent information to the user. In some embodiments, the disclosed system may provide an augmented reality environment for users to use.

The system disclosed herein is suitable for peer-to-peer learning where neither the learner nor the reviewer needs to have significant expertise in the skill. Applicant has tested the disclosed system in a gym class setting and has obtained effective results. The test results show that students can spend more time performing the skill by avoiding the bottleneck of lining up and waiting to perform the skill one-by-one in front of the coach. Consensus evaluation has been successfully used in a classroom setting to lead group discussion, opinion, and review of skill performance. The test results also show students' acts of evaluating their peers are effective as learning-by-teaching. The learning is effective even when the reviewers are not experts. Students learn to be proficient more quickly.

In some embodiments, the structured human movement library is initially absent or partially populated, and a relatively unskilled learner constructs and populates the structured human movement library themselves as a learning and skill deconstruction technique.

In some embodiments, the system may provide the necessary tools to enable such user-created content to be re-used privately or publically in a local setting and a non-local setting.

According to one aspect of this disclosure, there is provided a system for assessing user performance. The system comprises a server comprising a database storing therein a library, said library comprising at least a plurality of reference images illustrating a plurality of skill components, said plurality of reference images being organized in a hierarchical structure in accordance with the plurality of skill components; an imaging device; and a first assessment device comprising a processing structure coupled to an input interface, a network interface and a display, the first assessment device coupled to the imaging device and being configured for communicating with the server via the network interface thereof for accessing the database. The processing structure of the first assessment device is configured for retrieving from the library one or more first reference images illustrating one or more first skill components of the plurality of skill components; commanding the imaging device to capture at least one or more images of a user performing the one or more skill components; concurrently displaying the one or more first reference images and the one or more captured images for comparison; and receiving from the input interface of the first assessment device an assessment result of the user's performance for each of the one or more first skill components.

In some embodiments, said one or more first reference images comprise a plurality of first reference images forming a reference video clip; and wherein said one or more captured images comprise a plurality of captured images forming a captured video clip.

In some embodiments, said library also comprises one or more audio clips.

In some embodiments, the processing structure of the first assessment device is further configured for determining the difference between the one or more first reference images and the one or more captured images.

In some embodiments, said step of determining the difference comprises determining the difference between the one or more first reference images and the one or more captured images by using motion analysis and pattern recognition.

In some embodiments, the system further comprises one or more second assessment devices each comprising a processing structure and an input interface. The processing structure of each second assessment device is configured for receiving from the input interface thereof an assessment result of the user's performance for each of the one or more first skill components.

In some embodiments, each of the one or more second assessment devices further comprises a network interface and a display. The processing structure of the first assessment device is further configured for transmitting the one or more captured images to the one or more second assessment devices. The processing structure of each second assessment device is further configured for receiving the one or more captured images; and displaying the received one or more captured images on the display thereof.

In some embodiments, the processing structure of the first assessment device is further configured for transmitting the one or more first reference images to the one or more second assessment devices. The processing structure of each second assessment device is further configured for receiving the one or more first reference images; and displaying the received one or more first reference images on the display thereof.

In some embodiments, the one or more second assessment devices are configured for communicating with the server via the network interface thereof for accessing the database. The processing structure of the first assessment device is further configured for transmitting an indication of the one or more first reference images to the one or more second assessment devices. The processing structure of each second assessment device is further configured for receiving the indication of the one or more first reference images; retrieving the one or more first reference images from the library by using said indication; and displaying the received one or more first reference images on the display thereof.

In some embodiments, the processing structure of each of the first and second assessment devices is configured for transmitting the assessment results thereof to the server. The server is configured for receiving the assessment results; and analyzing the received assessment results for generating analytical results with respect to the one or more first skill components.

In some embodiments, said analyzing the received assessment results comprises digitizing the received assessment results; summing the digitized assessment results for each of the one or more skill components to obtain an assessment value for each of the one or more skill components; and normalizing the summed assessment values to obtain normalized assessment values.

In some embodiments, said analyzing the received assessment results further comprises presenting the normalized assessment values as a chart.

According to one aspect of this disclosure, there is provided a method for assessing user performance. The method comprises retrieving from a library in a database one or more first reference images illustrating one or more first skill components of the plurality of skill components; capturing at least one or more images of a user performing the one or more skill components; concurrently displaying on a first assessment device the one or more first reference images and the one or more captured images for comparison; and receiving from the first assessment device an assessment result of the user's performance for each of the one or more first skill components.

According to one aspect of this disclosure, there is provided a method of generating a tool for assessing a user performance. The method comprises recording a plurality of images of a reference performance; associating the plurality of images with one or more skill components, the one or more skill components being associated with a skill in a hierarchical structure; and for each of the one or more skill components, determining a position of the skill component in the hierarchical structure, associating the images associated with the skill component with the hierarchical structure at the determined position thereof, and storing the hierarchical structure in the database.

According to one aspect of this disclosure, there is provided a computer-readable storage device comprising computer-executable instructions for assessing user performance, wherein the instructions, when executed, cause a processing structure to perform actions comprising retrieving from a library in a database one or more first reference images illustrating one or more first skill components of the plurality of skill components; capturing at least one or more images of a user performing the one or more skill components; concurrently displaying on a first assessment device the one or more first reference images and the one or more captured images for comparison; and receiving from the first assessment device an assessment result of the user's performance for each of the one or more first skill components.

According to one aspect of this disclosure, there is provided a computer-readable storage device comprising computer-executable instructions for generating a tool for assessing a user performance, wherein the instructions, when executed, cause a processing structure to perform actions comprising recording a plurality of images of a reference performance; associating the plurality of images with one or more skill components, the one or more skill components being associated with a skill in a hierarchical structure; and for each of the one or more skill components, determining a position of the skill component in the hierarchical structure, associating the images associated with the skill component with the hierarchical structure at the determined position thereof, and storing the hierarchical structure in the database.

DETAILED DESCRIPTION

System Structure

Figure 1:
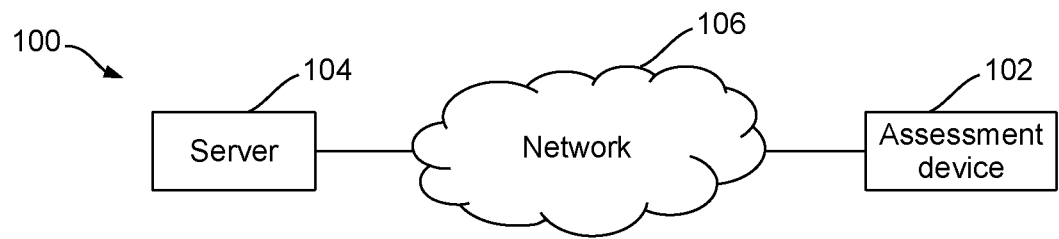
FIG. 1 is a schematic diagram of a performance learning system, according to some embodiments of this disclosure.

Turning now to FIG. 1, a performance learning system 100 is shown. The performance learning system 100 in this embodiment comprises an assessment device 102 functionally connected to one or more servers 104 via a network 106. The connection between the assessment device 102 and the network 106 may be any suitable wired or wireless connection means such as Ethernet, (WI-FI is a registered trademark of Wi-Fi Alliance, Austin, Tex., USA), BLUETOOTH® (BLUETOOTH is a registered trademark of Bluetooth Sig. Inc., Kirkland, Wash., USA), ZIGBEE® (ZIGBEE is a registered trademark of ZigBee Alliance Corp., San Ramon, Calif., USA), 3G or 4G or 5G wireless telecommunications, and the like, and is preferably a suitable wireless connection means.

The assessment device 102 is a computing device having an imaging device or component such as a camera integrated therein or separated therefrom but functionally coupled thereto. For example, in various embodiments, the assessment device 102 may be a desktop computer, a laptop computer, a tablet device with a touch-sensitive screen, a smartphone, a personal digital assistant (PDA), a virtual reality device (VR), an augmented reality device (AR), a speaker, a smart speaker, or the like. Preferably, the assessment device 102 is a portable computing device such as a laptop computer, a tablet device, a smartphone, a personal digital assistant (PDA), or the like.

Figure 2:
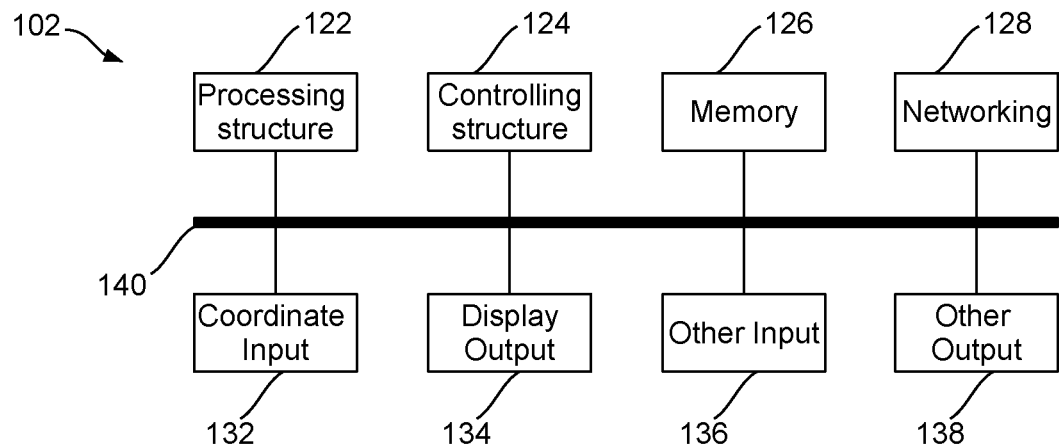
FIG. 2 is a schematic diagram showing the hardware structure of an assessment device of the performance learning system shown in FIG. 1.

FIG. 2 shows the hardware structure of the assessment device 102. As shown, the assessment device 102 comprises a processing structure 122, a controlling structure 124, memory or storage 126, a networking interface 128, coordinate input 132, display output 134, a camera 136, and other input and output modules 138, all functionally interconnected by a system bus 140.

The processing structure 122 may be one or more single-core or multiple-core computing processors such as Intel® microprocessors (INTEL is a registered trademark of Intel Corporation of Santa Clara, Calif., USA), AMD® microprocessors (AMD is a registered trademark of Advanced Micro Devices of Sunnyvale, Calif., USA), ARM® microprocessors (ARM is a registered trademark of ARM Ltd. of Cambridge, UK), or the like.

The controlling structure 124 comprises a plurality of controllers, such as graphic controllers, input/output chipsets, and the like, for coordinating operations of various hardware components and modules of the assessment device 102.

The memory 126 comprises a plurality of memory units accessible by the processing structure 122 and the controlling structure 124 for reading and/or storing data, including input data and data generated by the processing structure 122 and the controlling structure 124. The memory 126 may be volatile and/or non-volatile, non-removable or removable memory such as RAM, ROM, EEPROM, solid-state memory, hard disks, CD, DVD, flash memory, or the like. In use, the memory 126 is generally divided to a plurality of portions for different use purposes. For example, a portion of the memory 126 (denoted as storage memory herein) may be used for long-term data storing of files or databases. Another portion of the memory 126 may be used as the system memory for storing data during processing (denoted as working memory herein).

The networking interface 128 comprises one or more networking modules for connecting to other computing devices or networks via wired or wireless connections such as Ethernet, WIFI®, BLUETOOTH®, wireless phone channels, ZIGBEE®, or the like. In some embodiments, parallel ports, serial ports, USB connections, optical connections, or the like may also be used for connecting other computing devices or networks although they are usually considered as input/output interfaces for connecting input/output devices.

The display output 134 comprises one or more display modules for displaying images, such as monitors, LCD displays, LED displays, projectors, and the like. The display output 134 may be a physically integrated part of the assessment device 102 (for example, the display of a laptop computer or tablet), or alternatively, may be a display device physically separate from but functionally coupled to other components of the assessment device 102 (for example, the monitor of a desktop computer).

The coordinate input 132 comprises one or more input modules for one or more users to input coordinate data, such as touch-sensitive screen, touch-sensitive whiteboard, trackball, computer mouse, touch-pad, or other human interface devices (HID), and the like. The coordinate input 132 may be a physically integrated part of the assessment device 102 (for example, the touch-pad of a laptop computer or the touch-sensitive screen of a tablet), or may be a display device physically separate from but functionally coupled to other components of the assessment device 102 (for example, a computer mouse). The coordinate input 132, in some implementations, may be integrated with the display output 134 to form a touch-sensitive screen or touch-sensitive whiteboard.

The camera 136 may be an integrated camera component of the assessment device 102 (such as a camera component in a mobile phone or tablet computer) or alternatively, an independent camera device (such as a video camera) separate from but functionally connected to the assessment device 102 for capturing a learner's movement (described in more detail later). The camera 136, or assessment device 102 if the camera 136 is integrated therein, may include a support such as a stand or a tripod so that it can record the learner's movement unattended, for example, during self-assessment of an activity. The camera 136 may be held by another person for example, during peer-to-peer assessment.

In some embodiments, the camera 136 may also include one or more angle and movement sensors which also record data on the position, movement, and orientation of the recorder itself. In the case of video recording, this allows the video to be augmented with reference gridlines such as a horizontal grid or a vertical grid, and allows the human movement to be located in three-dimensional space.

In some embodiments, the system 100 may comprise more than one camera 136 and, in the case of video recording, multiple viewpoints of the human movement may be recorded.

In some embodiments, the camera 136 may also comprise other suitable components such as virtual reality cameras and sensors; augmented reality cameras and sensors; passive or active optical markers on the human, on specific body parts, or on sports or activity equipment; timing devices, stopwatches, laser trip timers; human movement sensors such as tilt sensors (for example, affixed to a learner's shoulder during performance of ballet movements), flex sensors (for example, affixed to a learner's back during performance of box lifting), accelerometers (for example, on the hand for a karate punch); force sensors such as force plates or equipment load cells; and/or the like.

In some embodiments, the camera 136 or some of its components are incorporated into or onto a piece of sports equipment or activity equipment.

Referring again to FIG. 2, the assessment device 102 may also comprise other input/output components 138 such as keyboards, microphones, scanners, speakers, printers, and the like.

The system bus 140 interconnects the various components 122 to 138 enabling them to transmit and receive data and control signals to/from each other.

Figure 3:
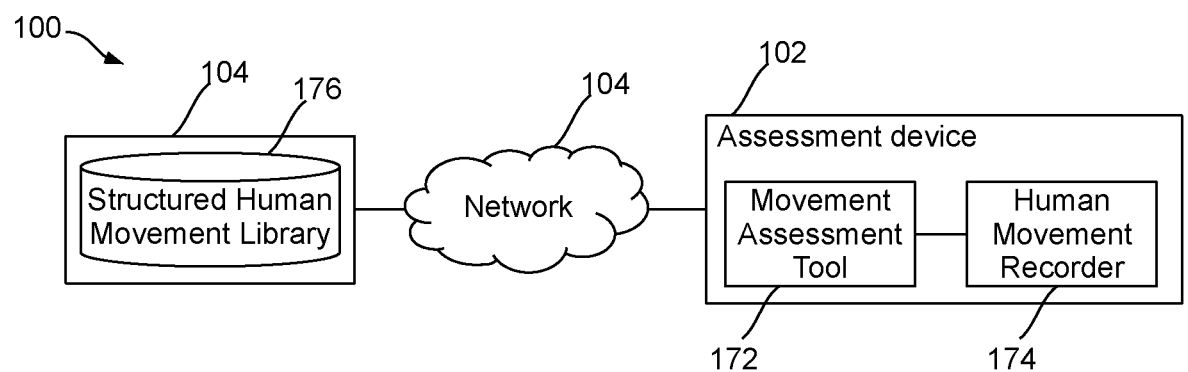
FIG. 3 is a schematic diagram showing the software structure of the performance learning system shown in FIG. 1.

FIG. 3 shows a software structure of the system 100. As illustrated, the assessment device 102 comprises a peer-to-peer or a self-directed movement assessment tool 172 functionally connected to a human movement recorder 174, and is functionally connected via the network 106 to a structured human movement library 176 by the one or more servers 104.

Although not shown, in some embodiments, the assessment device 102 may also comprise a system monitoring and feedback tool.

The human movement recorder 174 is a software interface for controlling the camera 136 to record the movement of one or more learners who is/are learning an activity.

Structured Human Movement Library

The Structured Human Movement Library 176 is a content management system with a library, such as a database, of illustrative human movements. These could, for example, be a video library of video clips of well-executed, exemplary human movements. The recordings do not need to be of experts, but are of human models with sufficient movement proficiency to achieve all the necessary movement steps or skill components for successful completion of the movement. For example, a proficient student performing the necessary sequence of skill components to complete a gymnastics cartwheel.

Alternative forms of the structured human movement library 176 can include video clips and/or animations of a human avatar completing the human movement skill, a stick figure animation, or a storyboard of illustrative still images, or a text description of the skill components.

Figure 4A:
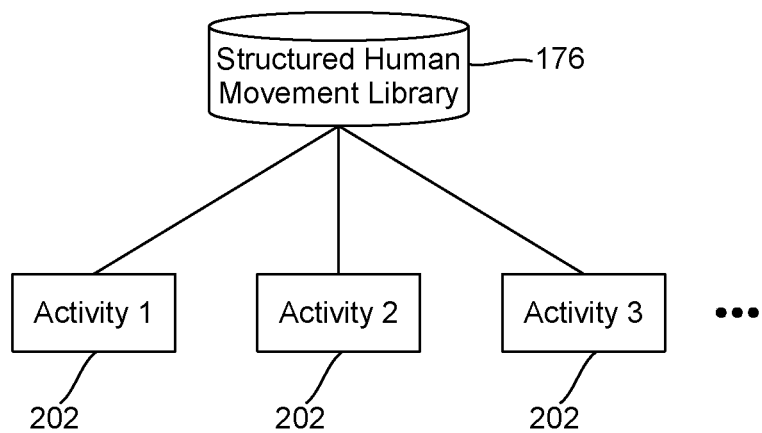
FIGS. 4A and 4B are schematic diagrams showing the hierarchical structure of a structured human movement library of the performance learning system shown in FIG. 1.
Figure 4B:
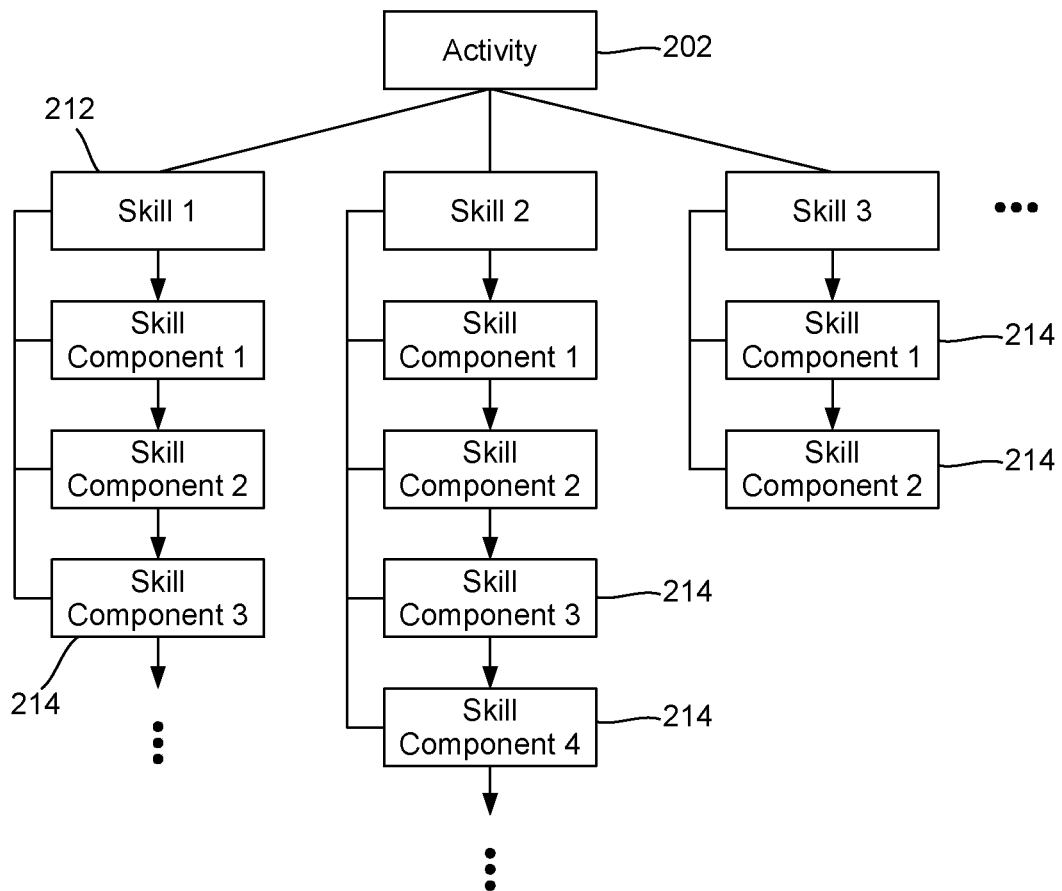

As shown in FIGS. 4A and 4B, a key feature of the structured human movement library 176 is that it has a hierarchical organization with one or more activities 202 at a highest level (see FIG. 4A). Examples of these activities 202 include: Basketball, Soccer, Occupational Health and Safety, First Aid, Rehabilitation, Canoeing, Ballet, Lacrosse, Gymnastics, Swimming, Orchestral Conducting, Drumming, and the like.

Organized at a subsequent level are one or more skills 212 necessary for competence in the activity 202. For example, organized within the Gymnastics Activity, the skills could include: Forward Roll, Backward Roll, Handstand, Cartwheel, Round-Off, Front Walkover, Back Walkover, Front Handspring, Front Tuck, Back Layout, Front Pike, Side Leap, and the like.

The third tier of the structured human movement library 176 is the specific skill Components 214 which are necessary for successful completion of the skill 212.

In one example of the structured human movement library 176, the activities 202 comprise Occupational Health & Safety, and the Skills 212 comprise Lifting a Box. The skill components 214 comprise:

1. Feet and shoulder width apart
2. One foot is slightly ahead of the other
3. When squatting, bend at the hips and knees only
4. Back is straight
5. Chest is out and shoulders are back
6. Straighten knees and hips to lift
7. Box is close to body In another example of the structured human movement library 176, the activities 202 comprise Ballet, and the skills 212 comprise Pirouette in 4th Position. The skill components 214 comprise:

1. Prep is turned out
2. Arms are open in prep
3. Heel is on the ground in the prep
4. Passé is in front of the supporting knee by the first ¼ turn
5. Arms are closed in turn
6. Turning leg remains straight In some embodiments, the skills 212 within an activity 202 can be aligned with standardized skill sets for national sports organizations.

In some embodiments, the skills 212 within an activity 202 may be rated for difficulty.

In some embodiments, the skills 212 within an activity 202 may be arranged in the form of a curriculum with a recommended sequence or progression of difficulty.

The framework of the structured human movement library 176 allows for easy addition of new content, in a format that allows for effective teaching.

The structured human movement library 176 may be constructed by a content creator such as an instructor, coach, or expert as follows:

An Instructor, Coach, or Expert in a given field (Activity) breaks the Activity into a series of Skills and then further breaks the Skills into components.

A simple question is identified for each skill component (e.g. "Feet and shoulder width apart?", "One foot is slightly ahead of the other?")

Each skill is performed by a model under the guidance of the instructor, coach or expert(s), and photographs and/or a video recorded of the performance.

If necessary, the video is broken down into still images matching the skill components and question.

Each image is properly annotated to identify key aspects. (e.g. arrow showing eyes looking forward)

Skills and images are entered into the database 176 by Activity.

In some cases, it may be effective for unskilled learners to construct the Structured Human Movement Library themselves by deconstructing a skill into individual skill components in the manner described above. This process of skill deconstruction allows a learner to demonstrate their understanding of the core components to a skill even before they are proficient at execution of the skill.

Figure 5:
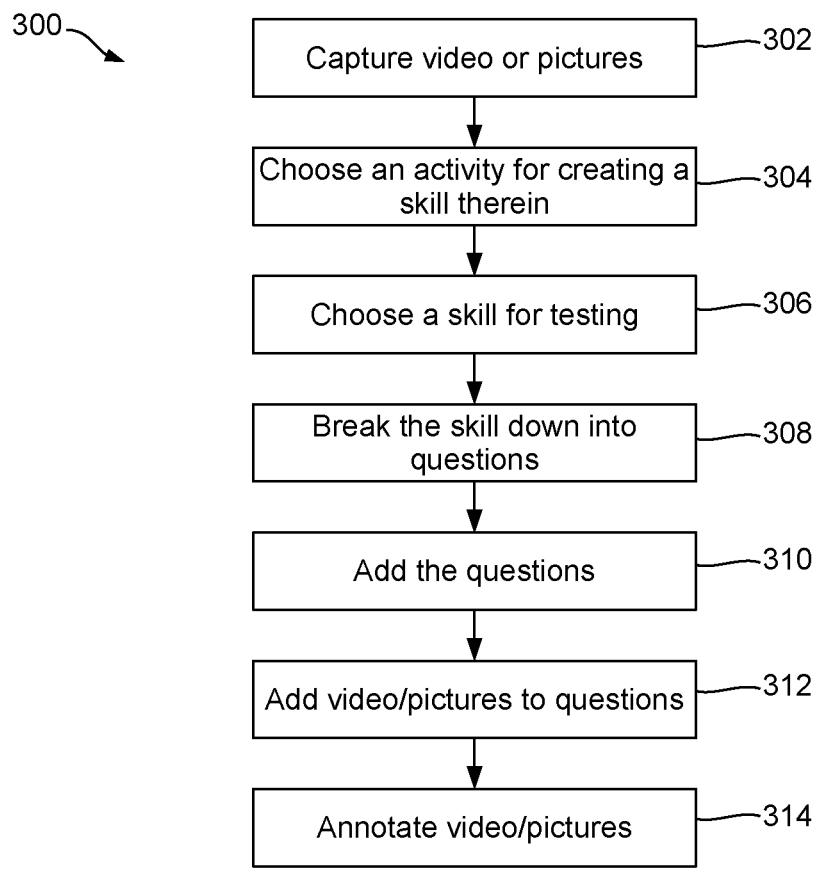
FIG. 5 is a flowchart showing a process for constructing the structured human movement library.

FIG. 5 is a flowchart showing a process 300 for constructing the structured human movement library 176. FIGS. 6A to 6F show an example of creating a basketball dribbling skill in the structured human movement library.

Figure 6A:
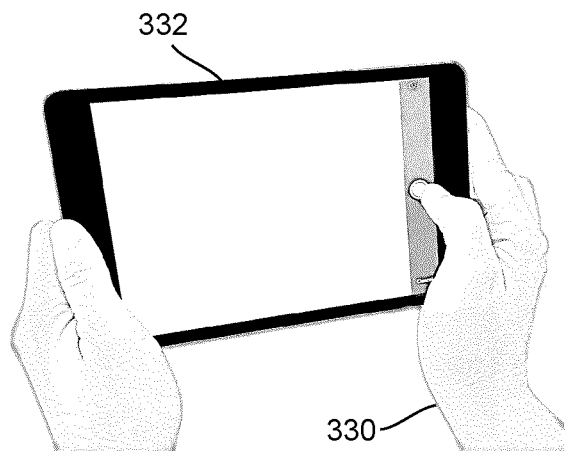
FIGS. 6A to 6F show an example of creating a basketball dribbling skill in the structured human movement library, following the flowchart shown in FIG. 5.

At step 302 and referring to FIG. 6A, the content creator 330 captures one or more videos and/or one or more pictures using a suitable imaging device 332 such as a camera, a tablet having an integrated camera, a smartphone having an integrated camera, and/or the like. Those skilled in the art will appreciate that step 302 is optional and in some alternative embodiments, the function of capturing videos and/or pictures may be combined into other suitable step such as step 312 (described later).

Figure 6B:
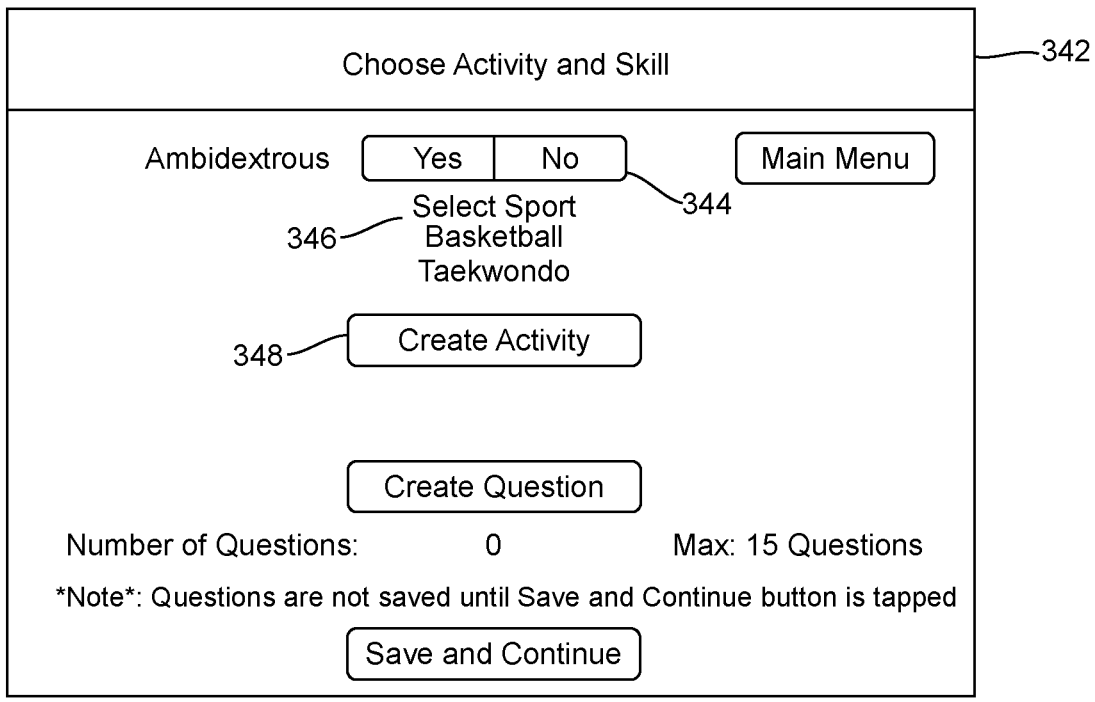
Figure 6C:
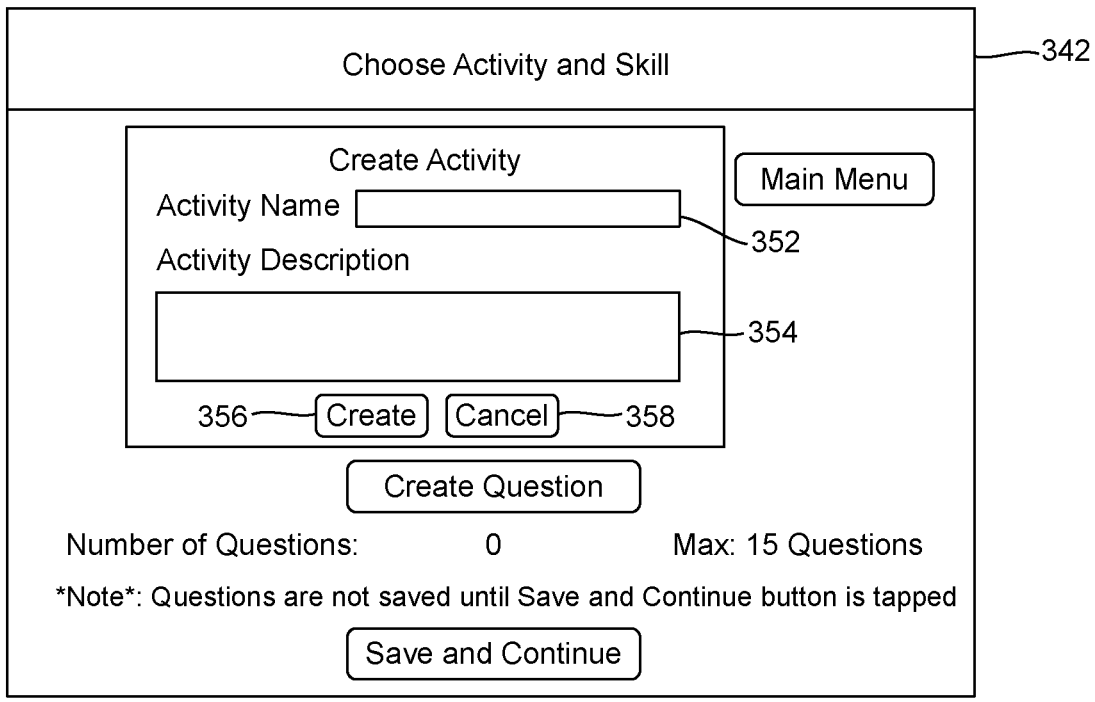

At step 304 and referring to FIG. 6B, the content creator 330 may choose an activity for creating a skill therein, by using a content creation user interface (UI) 342 of a computing device which may be the assessment device 102. As shown in FIG. 6B, the content creator (not shown) may choose whether the activity is ambidextrous 344, select a sport 346, and click or tap a "create activity" button 348. As shown in FIG. 6C, the content creator 330 may use the UI 342 to input an activity name 352, description of the activity 354, and then click or tap the "create" button 356 to create the activity. Of course, the content creator 330 may alternatively click or tap the "cancel" button to go back to the previous screen as shown in FIG. 6B without creating any activity.

Figure 6D:
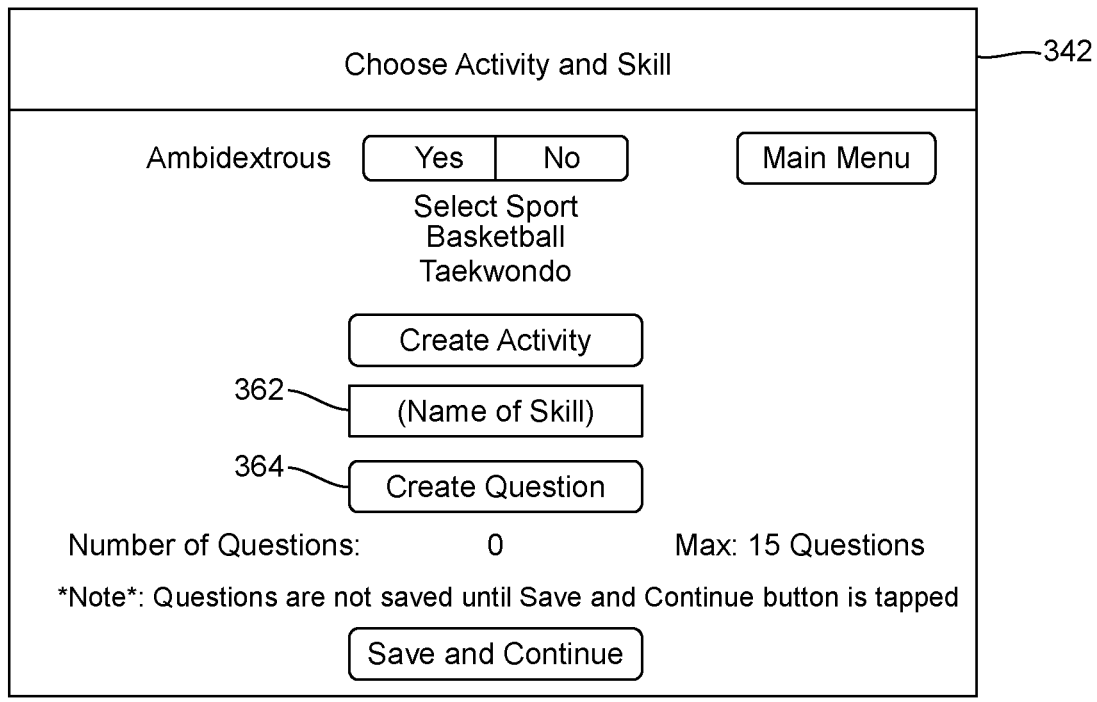

At step 306 and referring to FIG. 6D, the content creator 330 may choose a skill for testing, by entering a name of the skill into the text box 362 of the UI 342 and then click or tap the "create question" button 364.

At step 308, the content creator 330 breaks the skill down to a plurality of questions. For example, for the skill of basketball dribbling, the content creator 330 may break the skill down to the following questions:
  (i) Did your partner keep eyes up?
  (ii) Did your partner spread figures and use fingertips?
  (iii) Did your partner keep ball lower than waist level?
  (iv) Did your partner control ball at their side?
  (v) Did your partner protect ball using non-dribbling hand?
  (vi) Did your partner push the ball?

Figure 6E:
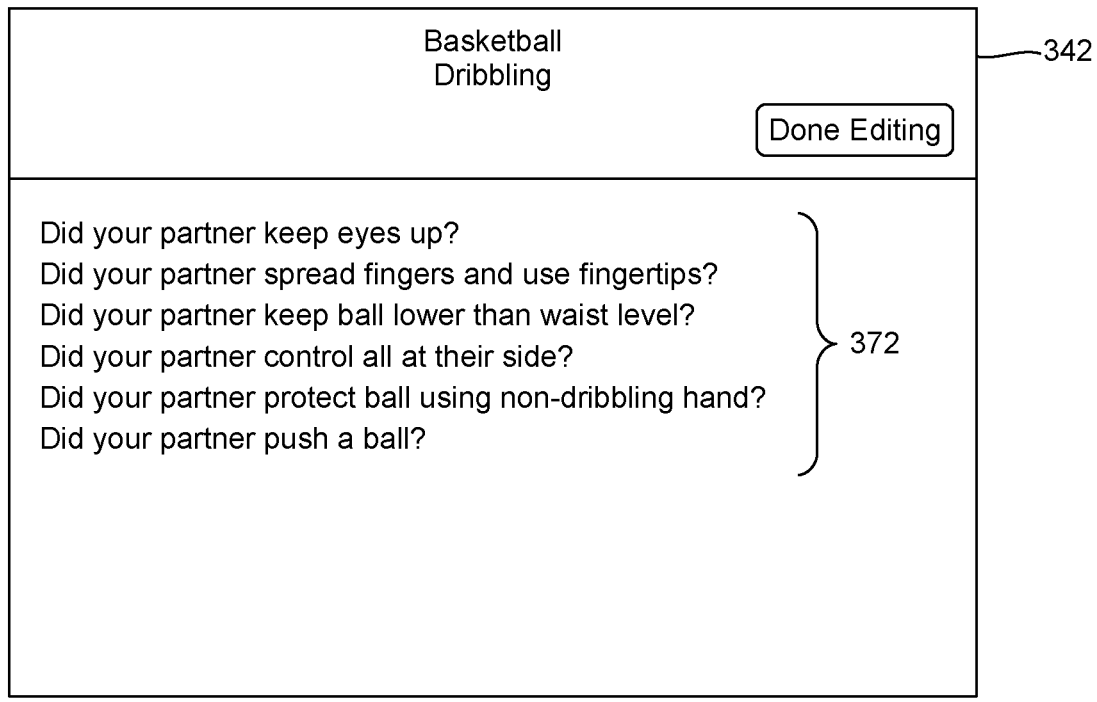

At step 310, the content creator 330 enters the questions via the UI 342. The entered questions 372 are shown in FIG. 6E.

Figure 6F:
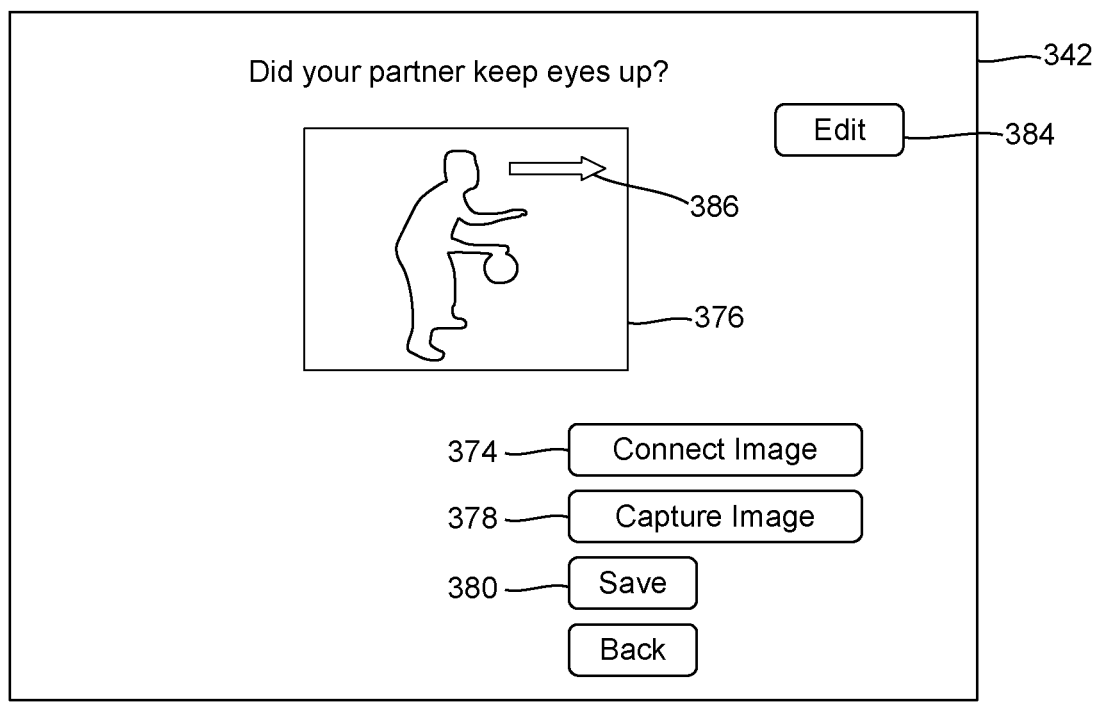

At step 312, the content creator 330 may click or tap each question 372 displayed on the UI 342 to add one or more videos and/or pictures. As shown in FIG. 6F, the content creator 330 may click or tap the "connect image" button 374 to import a previously generated video or image 376 such as the video or image generated at step 302. Alternatively, the content creator 330 may click or tap the "capture image" button 378 to capture a video or image 376.

At step 314 and referring to FIG. 6F, after the video or image 376 is loaded to the UI 342, the content creator 330 may click or tap the "edit" button 384 to annotate the imported video or image 376. FIG. 6F shows the annotated image 376 with annotation 386 overlaid thereon. The content creator 330 may click or tap the "save" button 380 to save the annotated image 376.

After all videos and/or pictures have been added and annotated as needed, the process 300 is terminated.

Figure 14:
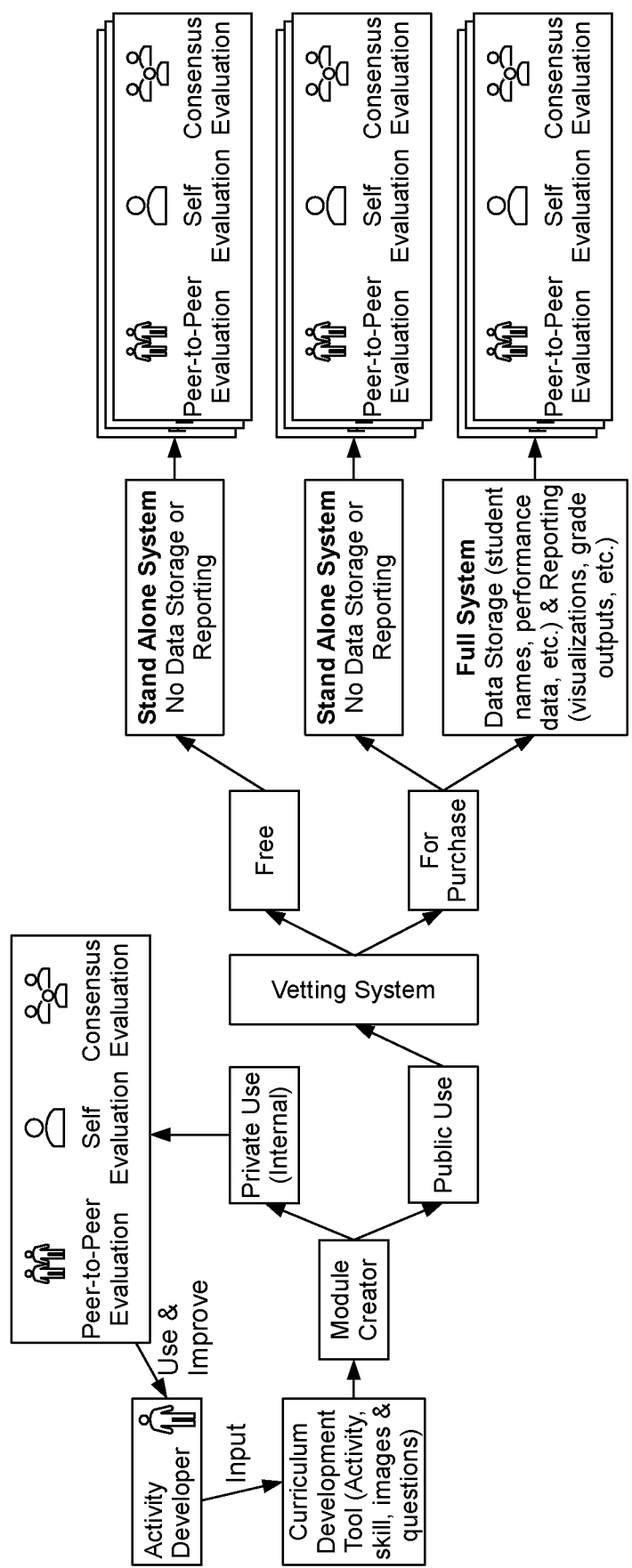
FIG. 14 is a schematic diagram showing the architecture of a performance learning system, according to some alternative embodiments of this disclosure.

FIG. 14 depicts an Activity Developer generating Activities, Skills, Images, and Questions for input into the Curriculum Development Tool (described in more detail later).
Peer-to-Peer or Self-Directed Movement Assessment Tool Referring again to FIG. 3, the peer-to-peer or self-directed movement assessment tool 172 is a program module for playback of the data recorded by the human movement recorder 174. The playback is presented together with the structured human movement library 176. In the case of video recording, the human movement video recording is played back alongside a text checklist corresponding to the skill components. The movement assessment tool 172 has the ability to collect user input from the person doing the movement assessment.

The movement assessment tool 172 thus allows a person, such as a reviewer, to use the movement assessment tool 172 to directly compare the performed human movement with the illustrative movement and assess compliance or non-compliance, and to input their assessment. The person doing the assessment (the reviewer) may be the learner themselves (self-assessment), their peer (peer-to-peer assessment), the coach (coach-evaluation), or a group of peers, coaches, and reviewers (consensus-assessment). The structure of the skill component checklist alongside the recording allows effective assessment by a person who is not necessarily an expert at the activity.

The movement assessment tool 172 may replay the recorded human movement as recorded, or it may process the recorded data to give modified or filtered data. For example, video recorded from multiple viewpoints may be interpolated to give artificial camera positions to more clearly depict the recorded human movement. Other examples of processing may include: slow motion, freeze-frame, video reversal, overlay of other sensor data, image enhancement, camera shake reduction, labelling, or silhouetting of the human for clarity or privacy.

The movement assessment tool 172 receives user input representing the assessment result of the recorded human movement. The format of the user input for the movement assessment tool 172 may be in the form of input buttons to assess successful completion of the skill component. Buttons may include "YES", "PARTIAL", and "NO".

In some embodiments, the movement assessment tool 172 may also receive input in the form of text commentary, audio commentary, and/or video commentary.

In some embodiments, the movement assessment tool 172 has navigation control to allow the Reviewer to move to other skill components. Similarly, the movement assessment tool 172 in some embodiments may have navigation controls for playback of the recorded human movement.

In some embodiments, the movement assessment tool 172 stores information about the reviewer's progression through the assessment. For example, the movement assessment tool 172 stores information about the timestamp of the video at which the reviewer was able to do the assessment. This can be useful for later review, confirmation, and feedback.

In some embodiments, the movement assessment tool 172 is in the form of a virtual reality or an augmented reality system.

In some embodiments, the movement assessment tool 172 may also comprise a consensus assessment module. In these embodiments, the performance learning system 100 may be used individually for self-assessment, in pairs with a single device for peer-to-peer assessment, or in groups for consensus assessment where multiple reviewers each complete an assessment of a single learner. In this case, the performance learning system 100 aggregates the assessments of each of the reviewers.

In some embodiments, a single assessment is generated based on the average response, modal response, or unanimity of response, or responses are averaged to give a fractional assessment of completion of the skill component.

The consensus evaluation can be used to improve or train or validate the observability of the reviewer, for example in the training of officials, umpires, referees, and the like.

In some embodiments, the human movement recorder 174 may be used to record the performance of a collective of people, such as a team. The skill components may then be measurements of an individual learner's performance or of the collective team's performance.
Feedback Tool In some embodiments, the performance learning system 100 also comprises a system monitoring and feedback tool.

The feedback tool is a tool for monitoring the quality of aspects of the overall system. For example, the feedback tool may be the same tablet computer with a screen for the learner to provide input, comments, or feedback on the effectiveness of the reviewer's in their accuracy, consistency, and manner. The feedback tool may alternatively be used by a coach or skilled instructor to monitor the quality, accuracy, and completeness of the reviewer's assessments.

In some embodiments, the system monitoring and feedback tool can allow one or more authorized instructors, coaches, or administrators to review the data collected to ensure quality and appropriateness.

Method of Use

Figure 7A:
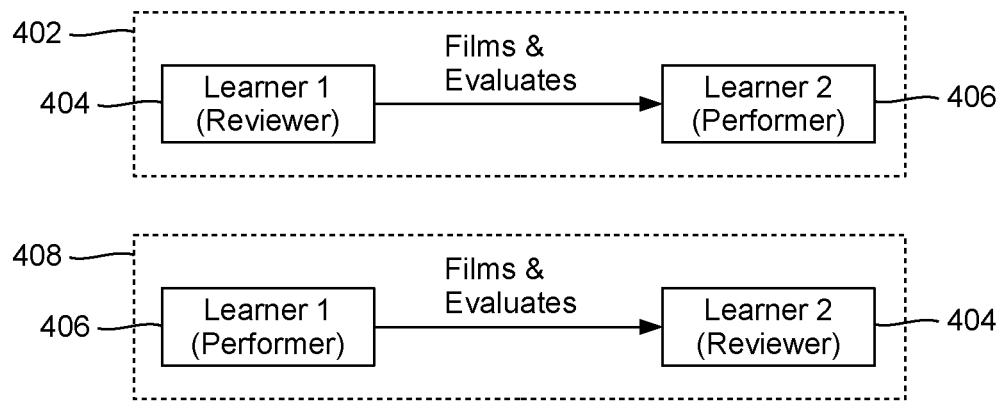
FIG. 7A is a schematic diagram showing a Peer-to-Peer learning and role reversal method using the performance learning system shown in FIG. 1.

In some embodiments, the performance learning system 100 is used for Peer-to-Peer learning and role reversal. As shown in FIG. 7A, in a first learning scenario 402, a first learner 404 may a reviewer and a second learner 406 may be a performer. The first learner 404 then films and evaluates the performance of the second learner 406.

In a second scenario 408, the second learner 406 may the reviewer and the first learner 404 may be the performer. The second learner 406 then films and evaluates the performance of the first learner 404.

Figure 7B:
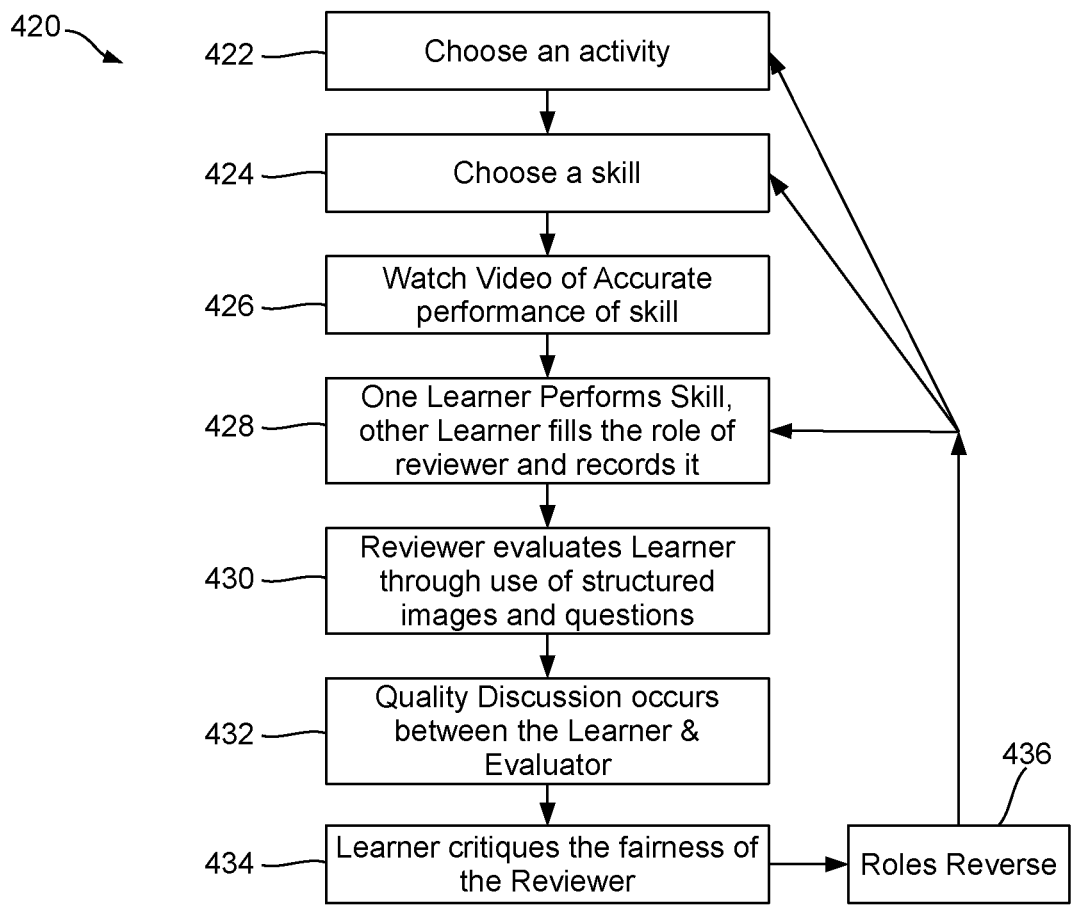
FIG. 7B is a flowchart showing a process of the Peer-to-Peer learning and role reversal method shown in FIG. 7A.

FIG. 7B shows a corresponding process 420 for Peer-to-Peer learning and role reversal. Following the process 420, two users may use the performance learning system 100 to learn a specific skill within an activity. A first of the two users acts as the learner and a second of the two users acts as the reviewer. The process 420 comprises the following steps:

Step 422: the reviewer uses the movement assessment tool 172 of the assessment device 102 to choose an Activity from the Library 176. In response, the library 176 provides a list of skills associated with the activity.

Step 424: the reviewer chooses the specific Skill to be evaluated.

Step 426: the reviewer is prompted by the movement assessment tool 172 with a recording of a model performing the specified skill. This provides the reviewer a reference of how to record the learner's performance in later step. It also provides initial instruction to the learner on how to perform the skill.

Step 428: the learner performs the skill and the reviewer uses the camera 136 (via the human movement recorder 174) to record the learner's performance.

Step 430: the reviewer is prompted by the movement assessment tool 172 to evaluate the Learner's performance of the skill on a component by component basis. The reviewer has the recording of the learner displayed concurrent with curriculum details of the skill component. Many skill components are evaluated for each skill (for example, 4 to 12 on average). The reviewer inputs the assessment result to the movement assessment tool 172 via an input interface of the assessment device 102.

Step 432: the reviewer is prompted by the movement assessment tool 172 to share the evaluation with the learner.

Step 434: the learner reviews the evaluation being presented by the movement assessment tool 172 with their own performance as well as the curriculum and the results of the reviewer's performance. Discussion may ensue between the learner and the reviewer at which point the reviewer can adjust their evaluation.

At this step, the learner is also prompted by the movement assessment tool 172 to rank the fairness of the reviewer.

Step 436: the reviewer then becomes the learner, and the process 420 may loop back to step 422, 424, or 428 as the users 404 and 406 desire for repeating the learning.

Figure 8A:
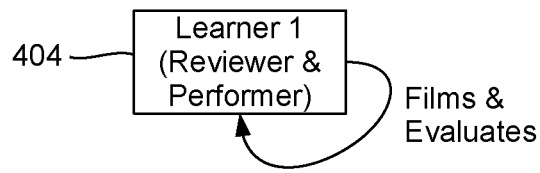
FIG. 8A is a schematic diagram showing a self-evaluation method using the performance learning system shown in FIG. 1.

In some embodiments as shown in FIG. 8A, the performance learning system 100 is used for self-evaluation where the user 404 acts as both the learner and the reviewer.

Figure 8B:
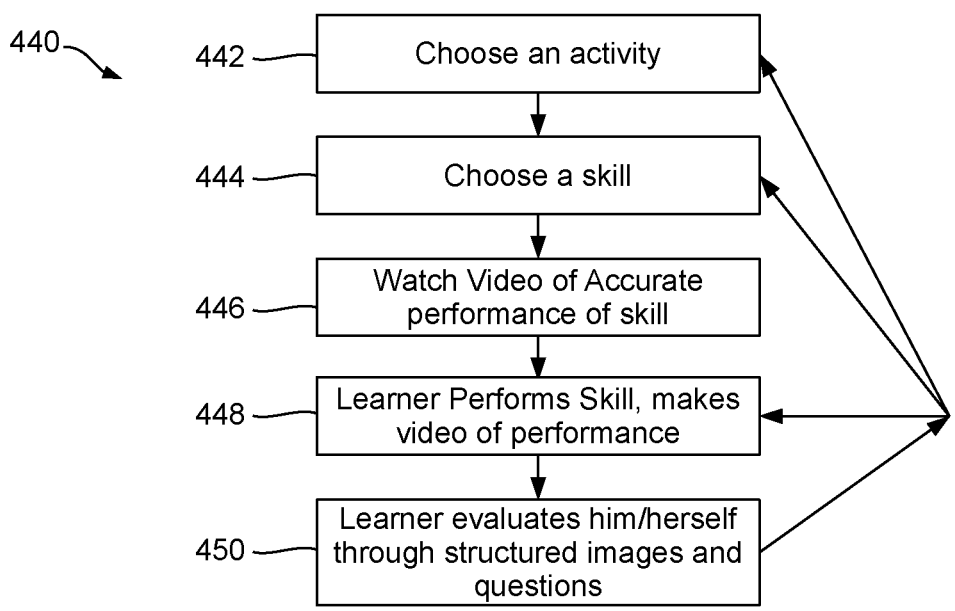
FIG. 8B is a flowchart showing a process of the self-evaluation method shown in FIG. 8A.

FIG. 8B shows a corresponding process 440 for self-evaluation which comprises the following steps:

Step 442: the user uses the movement assessment tool 172 of the assessment device 102 to choose an activity from the library 176. In response, the library 176 provides a list of skills associated with the activity.

Step 444: the user chooses the specific skill to be evaluated.

Step 446: the user is prompted by the movement assessment tool 172 with a recording of a model performing the specified skill. This provides the user a reference of how to record his/her performance in later step. It also provides initial instruction to the user on how to perform the skill.

Step 448: the user sets up the camera 136 at a location for recording and then performs the skill. The camera 136 (via the human movement recorder 174) records the user's performance.

Step 450: the user is prompted by the movement assessment tool 172 to evaluate his/her performance of the skill on a component-by-component basis. The user has the recording of his/her performance displayed concurrent with curriculum details of the skill component. Many skill components are evaluated for each skill. The user inputs the assessment result to the movement assessment tool 172 via an input interface of the assessment device 102.

Then, the process 440 may loop back to step 442, 444, or 448 as the user desires for repeating the learning.

Figure 9A:
FIG. 9A is a schematic diagram showing a method of using the performance learning system shown in FIG. 1 for evaluation or coaching by a coach.

In some embodiments as shown in FIG. 9A, the performance learning system 100 is used for a learner 404 to learn from a leader 452 such as a coach, instructor or teacher.

Figure 9B:
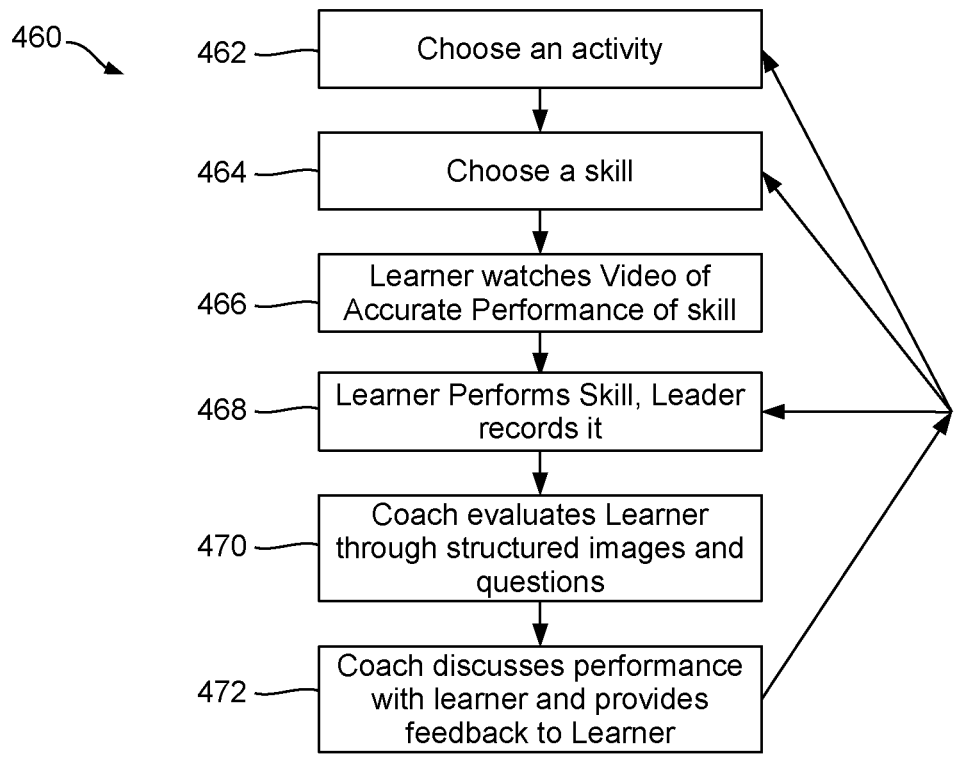
FIG. 9B is a flowchart showing a process of the coach-evaluation method shown in FIG. 9A.

FIG. 9B shows a corresponding process 460 for learning from the leader which comprises the following steps:

Step 462: the leader uses the movement assessment tool 172 of the assessment device 102 to choose an activity from the library 176. In response, the Library 176 provides a list of skills associated with the activity.

Step 464: the leader chooses the specific skill to be evaluated.

Step 466: the leader is prompted by the movement assessment tool 172 with a recording of a model performing the specified skill. This provides the leader a reference of how to record the learner's performance in later step. It also provides initial instruction to the learner on how to perform the skill.

Step 468: the learner performs the skill and the leader uses the camera 136 (via the human movement recorder 174) to record the learner's performance.

Step 470: the leader is prompted by the movement assessment tool 172 to evaluate the learner's performance of the skill on a component by component basis. The leader has the recording of the learner displayed concurrent with curriculum details of the skill component. Many skill components are evaluated for each skill. The leader inputs the assessment result to the movement assessment tool 172 via an input interface of the assessment device 102.

Step 472: the leader is prompted by the movement assessment tool 172 to share the evaluation with the learner, discusses the performance with learner, and provides feedback to learner.

Then, the process 460 may loop back to step 462, 464, or 468 as the learner and/or leader desire to repeat the learning.

Figure 10A:
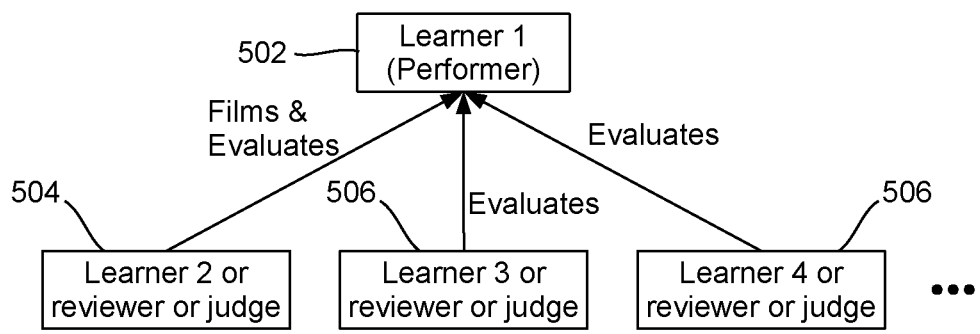
FIG. 10A is a schematic diagram showing a method of using the performance learning system shown in FIG. 1 for evaluation or coaching by a group using consensus learning.

In some embodiments as shown in FIG. 10A, the performance learning system 100 may be used for evaluation or coaching by a group of users using consensus learning.

As shown in FIG. 10A, a first learner 502 acts as the performer, a second learner 504 acts as a recorder for recording the performance of the performer 502 and also as a reviewer for evaluating the performance of the performer 502. One or more other learners 506 act as reviewers for evaluating the performance of the performer 502.

Figure 10B:
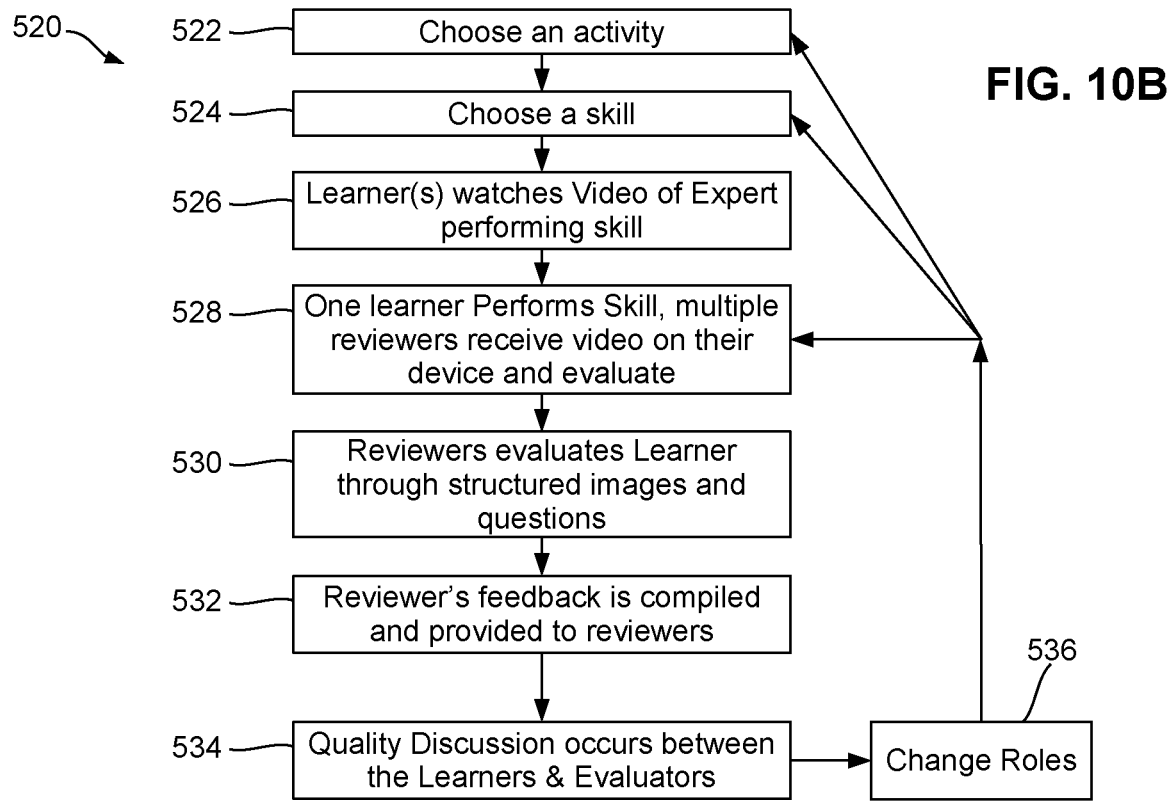
FIG. 10B is a flowchart showing a process of the consensus-evaluation method shown in FIG. 10A.

FIG. 10B shows a corresponding process 520 for group learning which comprises the following steps:

Step 522: one of the reviewers uses the movement assessment tool 172 of the assessment device 102 to choose an activity from the library 176. In response, the library 176 provides a list of skills associated with the activity.

Step 524: the reviewer chooses the specific skill to be evaluated.

Step 526: all reviewers are prompted by the movement assessment tool 172 with a recording of a model performing the specified skill. This provides the reviewers who would like to be the recorder a reference of how to record the performer's performance in later step. It also provides initial instruction to the reviewers on how to perform the skill.

Step 528: the performer performs the skill. The reviewer 504 acts as the recorder and uses the camera 136 (via the human movement recorder 174) to record the performer's performance. The recorded performance is then transmitted to the assessment devices 102 of all other reviewers 506. In some embodiments, the assessment device 102 of the Reviewer 504 also transmits an indication of the curriculum details of the skill component to the assessment device 102 of all other reviewers 506, and the assessment devices 102 of all other reviewers 506 use the indication to retrieve the curriculum details of the skill component (such as one or more images or one or more video clips) from the library 176. In some alternative embodiments, the assessment device 102 of the Reviewer 504 transmits the curriculum details of the skill component retrieved from the library 176 to the assessment devices 102 of all other reviewers 506.

Step 530: the reviewers 504 and 506 are prompted by the movement assessment tool 172 to evaluate the performer's performance of the skill on a component by component basis. Each reviewer has the recording of the performer displayed concurrent with curriculum details of the skill component. Many skill components are evaluated for each skill. Each reviewer inputs the assessment result to the movement assessment tool 172 via an input interface of the assessment device 102.

Step 532: the reviewers 504 and 506 are prompted by the movement assessment tool 172 to share the evaluation with the performer, discusses the performance with the performer and provides feedback to the performer.

Step 536: the group may change roles for example, re-assign the roles of performer, recorder and reviewers among the users of the group. Then, the process 520 may loop back to step 522, 524, or 528 as the users desire for repeating the learning.

Figure 11:
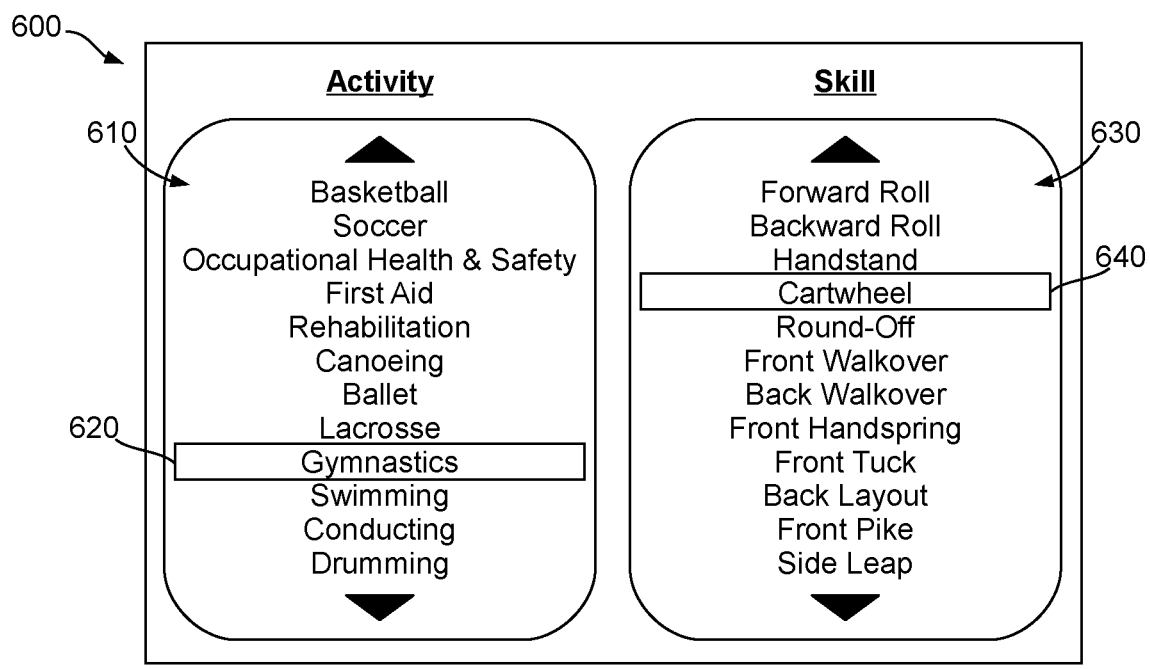
FIG. 11 shows an example of a user interface of the assessment device of the performance learning system shown in FIG. 1, wherein the user interface displays an Activity and Skill Selection screen.

FIG. 11 shows an example of a user interface of the assessment device 102 showing an activity and skill selection screen 600. In this embodiment, the assessment device 102 is a tablet device.

As shown in FIG. 11, the selection screen 600 shows a list of activities 610, and allows the user to select an activity 620. After the user selects the activity 620, the selection screen 600 shows a list of skills 630, and allows the user to select a skill component 640.

Figure 12:
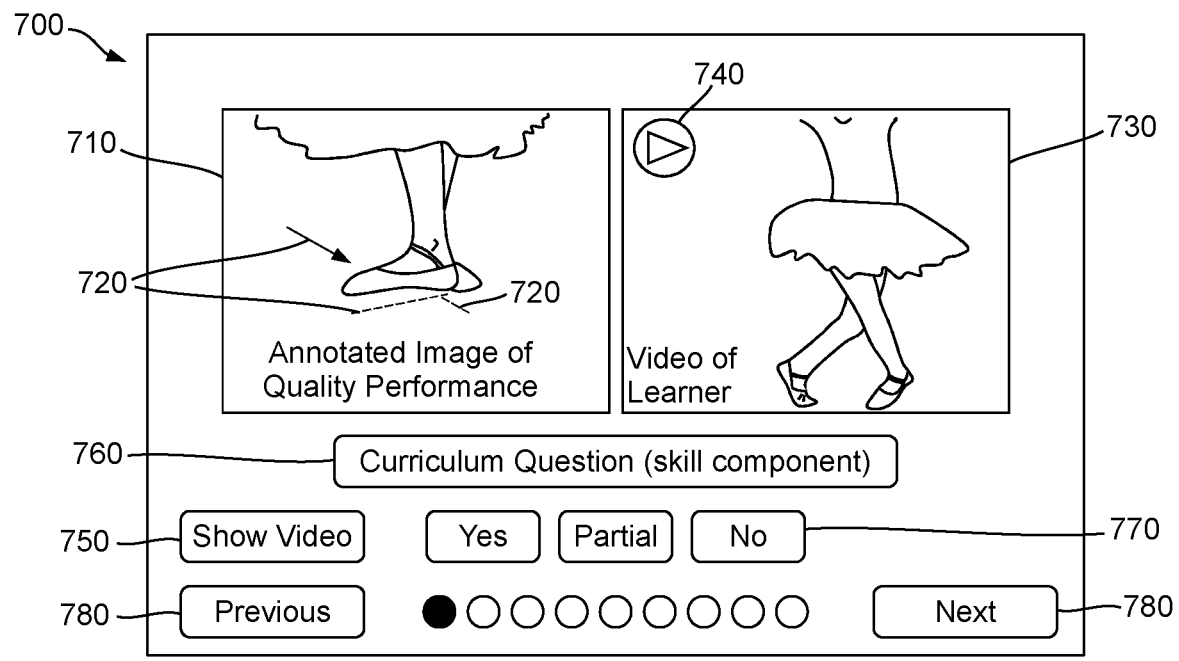
FIG. 12 shows an example of a user interface of the assessment device of the performance learning system shown in FIG. 1, wherein the user interface displays an evaluation screen.

FIG. 12 shows an example of the user interface of the assessment device 102 showing an evaluation screen 700. As shown, the evaluation screen 700 comprises a library image or video 710. The image may be annotated with a digital ink 720 to highlight important locations, angles, or directions. The evaluation screen 700 also shows the recorded human movement 730. The evaluation screen 700 may further include playback control 740 for the recorded human movement, and playback control 750 for the library video. The skill component includes a text description of an acceptable completion of the skill component in the form of a curriculum question 760. The evaluation screen includes reviewer response buttons 770, and skill component navigation buttons 780.

Figure 13:
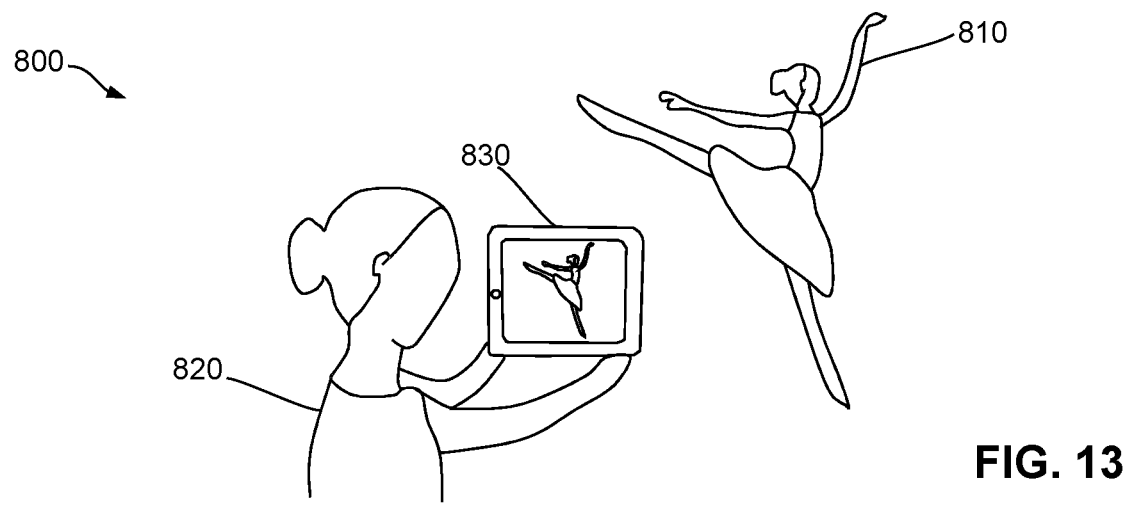
FIG. 13 shows an example of users using the performance learning system shown in FIG. 1 for Peer-to-Peer assessment.

FIG. 13 shows an example of a user using the performance learning system 100 for Peer-to-Peer assessment. A learner 810 is performing a skill while the reviewer 820 uses an assessment device, which in this example is a tablet device 830 with a camera (not shown), to record the human movement.

FIG. 14 is a schematic diagram showing the architecture of a performance learning system 900, according to some alternative embodiments of this disclosure. The performance learning system 900 allows a user to create their own modules that can be used internally, or distributed for public use at various levels of data collection and reporting.

Also shown within FIG. 14 is a private use case where the Structured Human Movement Library is used locally for self-evaluation, peer-to-peer evaluation, and consensus-evaluation. This private use mode is well suited for Structured Human Movement Library development by an unskilled learned as described above. Alternatively, this private use mode is well suited for iterative testing and refinement of the Structured Human Movement Library system.

In above embodiments, the structured human movement library 176 is hosted in one or more servers 104. The activities 202, skills 212, and skill components 214 of the structured human movement library 176 may be downloaded to assessment devices 202 as needed and subject to user access permissions.

Figure 15:
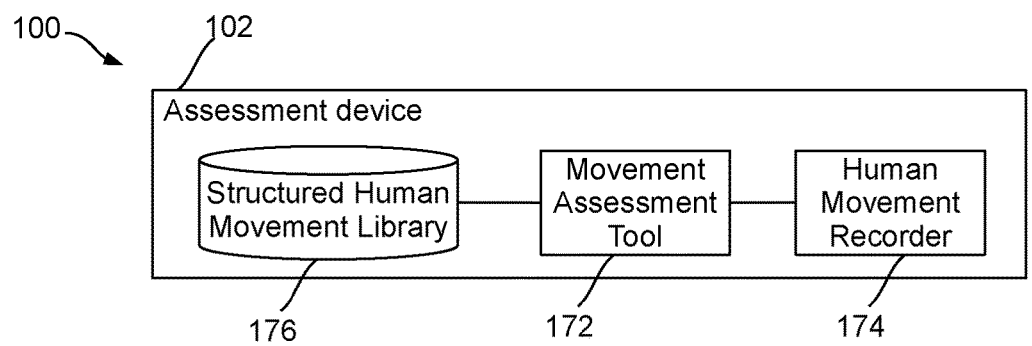
FIG. 15 is a schematic diagram of a performance learning system suitable for local use, according to some embodiments of this disclosure.

In some alternative embodiments as shown in FIG. 15, the performance learning system 100 only comprises an assessment device 102. The assessment device 102 comprises peer-to-peer or self-directed movement assessment tool 172, a human movement recorder 174, and a structured human movement library 176, functionally connected with each other.

Those skilled in the art will appreciate that, in various embodiments, the camera 136 may be any suitable imaging device, such as a two-dimensional (2D) camera capturing 2D videos and/or images, a three-dimensional (3D) camera capturing 3D videos and/or images, or a holographic camera capturing virtually 360 degrees videos and/or images.

Those skilled in the art will appreciate that, in various embodiments, the performance learning system 900 may include supporting systems, methods, hardware, and software to manage the secure storage of data. Such systems may include authentication, encryption, audit, and archiving methods. Such systems may additionally include anonymization methods.

Those skilled in the art will appreciate that, in various embodiments, the assessment device 102 may comprise any suitable display component or device for viewing the recording of the learner with a display of curriculum in visual, text, and audio forms prompting the reviewer to make an evaluation.

Those skilled in the art will appreciate that, in various embodiments, the system 100 may further comprise other suitable hardware and software components such as:

- Sensors that provides the reviewer stronger data and feedback against the curriculum to complete the evaluation;
- Augmented reality software module to show the curriculum over laid on the reality of the Learner; and/or
- Software module for the reviewer to notate and track specific points of interest through the skill performance (e.g., placing a dot on the tip of the finger and track through a volleyball serve, or on a person's hips to ensure they only travel in the vertical direction while lifting a box).

Although in above embodiments, images and/or videos are used for learning, in some alternative embodiments, the structured human movement library 176 may comprises audio clips or audio/video clips for learning. The assessment device 102 may record a learner's voice or the learner's video performance with voice for comparing with relevant audio clips or audio/video clips for learning.

Analytics Tool

Figure 16:
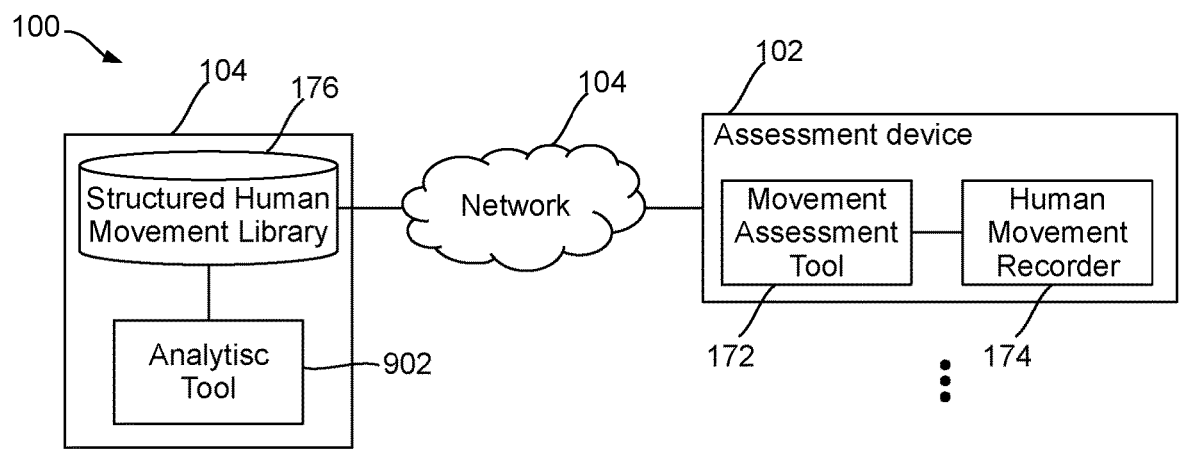
FIG. 16 is a schematic diagram of a performance learning system comprising an analytics tool, according to some embodiments of this disclosure.

In some embodiments as shown in FIG. 16, the performance learning system 100 also comprises an analytics tool 902 in the form of an application module running on a server 104. As shown, one or more assessment devices 102 store the assessment results in the database 176. The analytics tool 902 retrieves the assessment results from the database 176 and analyzes the human movement skill components performed by one or more Learners based on the retrieved assessment results.

In the analysis of the human movement, the analytics tool 902 digitizes the assessment results as needed. For example, in one embodiment, the assessment results are assessment options "YES", "PARTIAL", and "NO" that the Reviewers have selected for assessing the Learners' performances. The analytics tool 902 digitizes the assessment results by assigning each assessment option with a predefined value for example, "YES" with a value of three (3), "PARTIAL" with a value of two (2), and "NO" with a value of one (1).

Then, the analytics tool 902 sums the digitized assessment results with respect to various skill components to obtain a summed assessment value for each skill.

For example, in some embodiments, the analysis may be an analysis of a Learner's performance with respect to various skill components. In these embodiments, the analytics tool 902 sums the digitized assessment results of the Learner with respect to various skill components to obtain a summed assessment value for each skill component for the Learner.

Then, the analytics tool 902 may normalize each obtained assessment value for example, by dividing the summed assessment values by the maximum assessment value that the Leaner may receive from the Reviewers when performing the corresponding skill component.

For example, if there were ten (10) Reviewers assessing the Learner's performance of a skill component S_a with each Reviewer having three options "YES", "PARTIAL", and "NO", the maximum assessment value that the Leaner may receive from the ten Reviewers is 30.

On the other hand, if another five (5) Reviewers joined and the total number of Reviewers became fifteen (15) in assessing the Learner's performance of another skill component S_b with each Reviewer having three options "YES", "PARTIAL", and "NO", the maximum assessment value that the Leaner may receive from the ten Reviewers is 45.

The normalized assessment value of skill component S_a for the Learner is the Learner's summed assessment value divided by 30, and the normalized assessment value of skill component S_b for the Learner is the Learner's summed assessment value divided by 45.

Figure 17:
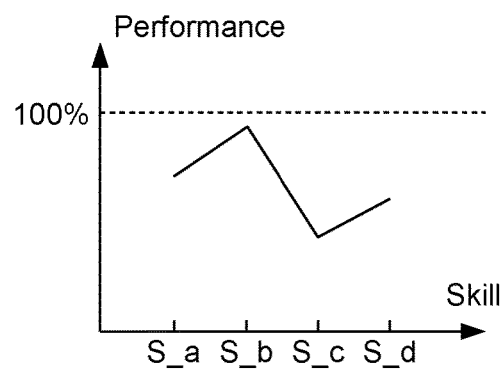
FIGS. 17 and 18 show performance charts generated by the analytics tool of the performance learning system shown in FIG. 16.

The normalized assessment values may be presented to the Learner for assisting the Learner to understand which skill components he/she has been performing well and which skill components need further improvement. Alternatively, the analytics tool 902 may generate a performance chart (see FIG. 17) using the normalized assessment values and present the performance chart to the Learner. The performance chart may be a line chart, a bar chart, or the like.

In some other embodiments, the analysis may be an analysis of the performances of a plurality of Learners as a group with respect to various skill components. In these embodiments, the analytics tool 902 sums the digitized assessment results of the plurality of Learners with respect to various skill components to obtain a summed assessment value for each skill component.

Then, the analytics tool 902 may normalize each obtained assessment value for example, by dividing the summed assessment values by the maximum assessment value that the corresponding skill component may receive from the Reviewers.

For example, if there were ten (10) Reviewers assessing ten (10) Learners' performance of a skill component S_a with each Reviewer having three options "YES", "PARTIAL", and "NO", the maximum assessment value that the skill component S_a may receive is 300.

On the other hand, if there were twenty (20) Reviewers in assessing twenty (20) Learners' performance of another skill component S_b with each Reviewer having three options "YES", "PARTIAL", and "NO", the maximum assessment value that the skill component S_b may receive is 1200.

The normalized assessment value of skill component S_a is the summed assessment value of skill component S_a divided by 300, and the normalized assessment value of skill component S_b is the Learner's summed assessment value divided by 1200.

Figure 18:
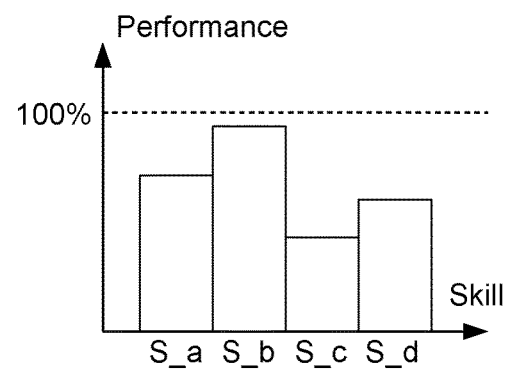

The normalized assessment values may be presented to a Reviewer or a coach for understanding which skill components are easy to learn and which skill components are difficult to learn. Alternatively, the analytics tool 902 may generate a performance chart (see FIG. 18) using the normalized assessment values and present the performance chart to the Reviewer or coach. The performance chart may be a line chart, a bar chart, or the like.

In above embodiments, the assessment options that a Reviewer may choose in assessing a Learner's performance include "YES", "PARTIAL", and "NO". In some alternative embodiments, the assessment options that a Reviewer may choose in assessing a Learner's performance only include "YES" and "NO". Experiments have shown that the two-assessment-option design (i.e., the design using "YES" and "NO" options) provides more reliable assessment results than designs using three or more options (e.g., the design using "YES", "PARTIAL", and "NO" options).

Although embodiments have been described above with reference to the accompanying drawings, those of skill in the art will appreciate that variations and modifications may be made without departing from the scope thereof as defined by the appended claims.

What is claimed is:

1. A system for assessing user performance, the system comprising:
   a server comprising a database storing therein a library, said library comprising at least a plurality of reference images illustrating a plurality of skill components organized in a hierarchical structure, said hierarchical structure comprising a plurality of activities, each activity comprising a plurality of the plurality of skill components, and each skill component comprising a plurality of the of reference images;
   an imaging device; and
   a first assessment device comprising a processing structure coupled to an input interface, a network interface and a display, the first assessment device coupled to the imaging device and being configured for communicating with the server via the network interface thereof for accessing the database;
   wherein the processing structure of the first assessment device is configured for:
   receiving from the input interface of the first assessment device one or more inputs indicating a selected one of the plurality of activities and one or more selected skill components of the selected activity;
   retrieving from the library selected one or more of the plurality of reference images based on the one or more selected skill components;
   commanding the imaging device to capture at least one or more images of a user performing the one or more selected skill components;
   concurrently displaying the selected one or more reference images and the one or more captured images for comparison; and
   receiving from the input interface of the first assessment device an assessment result of the user's performance for each of the one or more selected skill components.

2. The system of claim 1 further comprising:
   one or more second assessment devices each comprising a processing structure and an input interface;
   wherein the processing structure of each second assessment device is configured for receiving from the input interface thereof an assessment result of the user's performance for each of the one or more selected skill components.

3. The system of claim 2, wherein each of the one or more second assessment devices further comprises a network interface and a display;
   wherein the processing structure of the first assessment device is further configured for transmitting the one or more captured images to the one or more second assessment devices; and
   wherein the processing structure of each second assessment device is further configured for:
   receiving the one or more captured images; and
   displaying the received one or more captured images on the display thereof.

4. The system of claim 2, wherein the processing structure of each of the first and second assessment devices is configured for transmitting the assessment results thereof to the server; and
   wherein the server is configured for:
   receiving the assessment results; and
   analyzing the received assessment results for generating analytical results with respect to the one or more selected skill components.

5. The system of claim 4, wherein said analyzing the received assessment results comprises:
   digitizing the received assessment results;
   summing the digitized assessment results for each of the one or more selected skill components to obtain an assessment value for each of the one or more selected skill components; and
   normalizing the summed assessment values to obtain normalized assessment values.

6. The system of claim 1, wherein each assessment result comprises two assessment options only.

7. The system of claim 1, wherein said imaging device is a virtual-reality device or an augmented-reality device.

8. A method for assessing user performance, the method comprising:
   storing in a database a library comprising at least a plurality of reference images illustrating a plurality of skill components organized in a hierarchical structure, said hierarchical structure comprising a plurality of activities, each activity comprising a plurality of the plurality of skill components, and each skill component comprising a plurality of the of reference images;
   receiving from a first assessment device one or more inputs indicating a selected one of the plurality of activities and one or more selected skill components of the selected activity;
   retrieving from the library selected one or more of the plurality of reference images based on the one or more selected skill components;
   capturing at least one or more images of a user performing the one or more selected skill components;
   concurrently displaying on the first assessment device the selected one or more reference images and the one or more captured images for comparison; and
   receiving from the first assessment device an assessment result of the user's performance for each of the one or more selected skill components.

9. The method of claim 8 further comprising:
   receiving from one or more second assessment devices assessment results of the user's performance for each of the one or more selected skill components.

10. The method of claim 9 further comprising:
    collecting the assessment results; and
    analyzing the collected assessment results for generating analytical results with respect to the one or more selected skill components.

11. The method of claim 10, wherein said analyzing the collected assessment results comprises:
    digitizing the received assessment results;
    summing the digitized assessment results for each of the one or more selected skill components to obtain an assessment value for each of the one or more selected skill components; and
    normalizing the summed assessment values to obtain normalized assessment values.

12. The method of claim 8, wherein each assessment result consists of two assessment options only.

13. The method of claim 8, wherein said imaging device is a virtual-reality device or an augmented-reality device.

14. A computer-readable storage device comprising computer-executable instructions for assessing user performance, wherein the instructions, when executed, cause a processing structure to perform actions comprising:

storing in a database a library comprising at least a plurality of reference images illustrating a plurality of skill components organized in a hierarchical structure, said hierarchical structure comprising a plurality of activities, and each activity comprising a plurality of the plurality of skill components, and each skill component comprising a plurality of the of reference images;

receiving from a first assessment device one or more inputs indicating a selected one of the plurality of activities and one or more selected skill components of the selected activity;

retrieving from the library selected one or more of the plurality of reference images based on the one or more selected skill components;

capturing at least one or more images of a user performing the one or more selected skill components;

concurrently displaying on the first assessment device the selected one or more reference images and the one or more captured images for comparison; and receiving from the first assessment device an assessment result of the user's performance for each of the one or more selected skill components.

15. The computer-readable storage device of claim 14, wherein the instructions, when executed, further cause the processing structure to perform actions comprising:

determining the difference between the selected one or more reference images and the one or more captured images.

16. The computer-readable storage device of claim 14, wherein the instructions, when executed, further cause the processing structure to perform actions comprising:

receiving from one or more second assessment devices assessment results of the user's performance for each of the one or more selected skill components.

17. The computer-readable storage device of claim 16, wherein the instructions, when executed, further cause the processing structure to perform actions comprising:

collecting the assessment results; and analyzing the collected assessment results for generating analytical results with respect to the one or more selected skill components.

18. The computer-readable storage device of claim 17, wherein said analyzing the collected assessment results comprises:

digitizing the received assessment results;

summing the digitized assessment results for each of the one or more selected skill components to obtain an assessment value for each of the one or more selected skill components; and normalizing the summed assessment values to obtain normalized assessment values.

19. The computer-readable storage device of claim 14, wherein each assessment result consists of two assessment options only.

20. The computer-readable storage device of claim 14, wherein said capturing the at least one or more images of the user performing the one or more selected skill components comprising:

capturing the at least one or more images of the user performing the one or more selected skill components via an imaging device, a virtual-reality device, or an augmented-reality device.

* * * * *